(12) United States Patent
Householder et al.

(10) Patent No.: US 10,646,208 B2
(45) Date of Patent: May 12, 2020

(54) MARKER DELIVERY DEVICE FOR USE WITH MRI BREAST BIOPSY SYSTEM

(71) Applicant: Devicor Medical Products, Inc., Cincinnati, OH (US)

(72) Inventors: Robert M. Householder, Loveland, OH (US); Andrew P. Nock, Dayton, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 189 days.

(21) Appl. No.: 15/571,632

(22) PCT Filed: May 3, 2016

(86) PCT No.: PCT/US2016/030519
§ 371 (c)(1),
(2) Date: Nov. 3, 2017

(87) PCT Pub. No.: WO2016/179147
PCT Pub. Date: Nov. 10, 2016

(65) Prior Publication Data
US 2018/0140288 A1    May 24, 2018

Related U.S. Application Data

(60) Provisional application No. 62/157,604, filed on May 6, 2015.

(51) Int. Cl.
*A61B 10/02* (2006.01)
*A61B 17/00* (2006.01)
*A61B 90/00* (2016.01)

(52) U.S. Cl.
CPC ...... *A61B 10/0283* (2013.01); *A61B 10/0275* (2013.01); *A61B 2010/0208* (2013.01);
(Continued)

(58) Field of Classification Search
CPC ............ A61B 10/0283; A61B 10/0275; A61B 2090/3908; A61B 2090/3966;
(Continued)

(56) References Cited

U.S. PATENT DOCUMENTS 5,526,822 A    6/1996   Burbank et al.
5,928,164 A    7/1999   Burbank et al.
(Continued)

OTHER PUBLICATIONS

Hahn, Markus et al., "Vacuum Assisted Breast Biopsy with Mammotome®," available Nov. 11, 2012, copyright 2013 by Devicor Medical Germany GmbH, published in Germany by Springer Medizin Verlag. 128 pages.

(Continued)

*Primary Examiner* — Navin Natnithithadha
(74) *Attorney, Agent, or Firm* — Frost Brown Todd LLC

(57) ABSTRACT

A marker delivery device, "adaptor", for a MRI breast biopsy system is described and claimed. The marker adaptor for the MRI breast biopsy device provides the operator with the ability to easily mark after an MRI biopsy procedure through the biopsy sleeve. The flexible shaft marker snaps into the marking adaptor which creates the oval shape that mates with the inner surface of the sleeve. This locks the orientation of the sleeve and marker, with adaptor, together. The marker adaptor also contains a hard-stop which allows the user to place the biopsy marker in the correct location.

18 Claims, 23 Drawing Sheets

(52) U.S. Cl.
CPC ............. *A61B 2017/00004* (2013.01); *A61B 2017/0092* (2013.01); *A61B 2017/00907* (2013.01); *A61B 2090/3908* (2016.02); *A61B 2090/3966* (2016.02); *A61B 2090/3987* (2016.02)

(58) Field of Classification Search
CPC .... A61B 2090/3987; A61B 2010/0208; A61B 2017/00004; A61B 2017/00907; A61B 2017/0092
USPC ................ 600/562, 564, 565, 566, 567, 571
See application file for complete search history.

(56) References Cited

U.S. PATENT DOCUMENTS

| | | | |
|---|---|---|---|
| 6,017,316 A | 1/2000 | Ritchart et al. | |
| 6,086,544 A | 7/2000 | Hibner et al. | |
| 6,162,187 A | 12/2000 | Buzzard et al. | |
| 6,220,248 B1 | 4/2001 | Voegele et al. | |
| 6,270,464 B1 * | 8/2001 | Fulton, III | A61B 90/39 600/562 |
| 6,432,065 B1 | 8/2002 | Burdorff et al. | |
| 6,471,700 B1 * | 10/2002 | Burbank | A61B 10/0266 600/562 |
| 6,626,849 B2 | 9/2003 | Huitema et al. | |
| 6,699,205 B2 * | 3/2004 | Fulton, III | A61B 90/39 600/562 |
| 6,752,768 B2 | 6/2004 | Burdorff et al. | |
| 7,442,171 B2 | 10/2008 | Stephens et al. | |
| 7,507,210 B2 | 3/2009 | Hibner et al. | |
| 7,648,466 B2 | 1/2010 | Stephens et al. | |
| 7,831,290 B2 | 11/2010 | Hughes et al. | |
| 7,837,632 B2 | 11/2010 | Stephens et al. | |
| 7,854,706 B2 | 12/2010 | Hibner | |
| 7,914,464 B2 | 3/2011 | Burdorff et al. | |
| 7,938,786 B2 | 5/2011 | Ritchie et al. | |
| 8,050,742 B2 * | 11/2011 | Weizman | A61B 10/0275 600/420 |
| 8,068,895 B2 * | 11/2011 | Speeg | A61B 90/39 600/431 |
| 8,079,964 B2 * | 12/2011 | Reichel | A61B 90/39 424/1.25 |
| 8,083,687 B2 | 12/2011 | Parihar | |
| 8,118,755 B2 | 2/2012 | Hibner et al. | |
| 8,206,316 B2 | 6/2012 | Hibner et al. | |
| 8,241,226 B2 | 8/2012 | Hibner et al. | |
| 8,241,299 B2 * | 8/2012 | Hibner | A61B 90/39 600/562 |
| 8,251,916 B2 | 8/2012 | Speeg et al. | |
| 8,292,822 B2 * | 10/2012 | Fulton | A61B 90/39 600/526 |
| 8,371,443 B2 * | 2/2013 | Nock | A61B 90/39 206/363 |
| 8,454,531 B2 | 6/2013 | Speeg et al. | |
| 8,529,465 B2 * | 9/2013 | Speeg | A61B 10/0275 600/407 |
| 8,532,747 B2 | 9/2013 | Nock et al. | |
| 8,622,924 B2 | 1/2014 | Speeg et al. | |
| 8,702,623 B2 | 4/2014 | Parihar et al. | |
| 8,764,680 B2 | 7/2014 | Rhad et al. | |
| 8,801,742 B2 | 8/2014 | Rhad et al. | |
| 8,858,465 B2 | 10/2014 | Fiebig | |
| 8,938,285 B2 | 1/2015 | Fiebig et al. | |
| 9,095,326 B2 | 8/2015 | Ritchie et al. | |
| 9,326,755 B2 | 5/2016 | Fiebig et al. | |
| 9,345,457 B2 | 5/2016 | Speeg et al. | |
| 9,414,816 B2 * | 8/2016 | Rhad | A61B 10/0275 |
| 9,993,232 B2 * | 6/2018 | Ellingson | A61B 10/0266 |
| 9,999,406 B2 * | 6/2018 | Hibner | A61B 10/0275 |
| 10,010,380 B2 * | 7/2018 | Fulton | A61B 90/39 |
| 10,105,125 B2 * | 10/2018 | Shabaz | A61B 10/0275 |
| 10,172,595 B2 * | 1/2019 | Shabaz | A61B 10/0275 |
| 2004/0215187 A1 * | 10/2004 | Burbank | A61B 10/0266 606/45 |
| 2005/0065453 A1 * | 3/2005 | Shabaz | A61B 10/0266 600/564 |
| 2005/0159677 A1 * | 7/2005 | Shabaz | A61B 10/0275 600/567 |
| 2005/0283069 A1 | 12/2005 | Hughes et al. | |
| 2006/0074345 A1 | 4/2006 | Hibner | |
| 2007/0010738 A1 * | 1/2007 | Mark | A61B 90/39 600/427 |
| 2007/0016017 A1 * | 1/2007 | Mark | A61B 90/39 600/431 |
| 2008/0214955 A1 | 9/2008 | Speeg et al. | |
| 2009/0131821 A1 | 5/2009 | Speeg et al. | |
| 2009/0209854 A1 | 8/2009 | Parihar et al. | |
| 2009/0270725 A1 * | 10/2009 | Leimbach | A61B 10/0275 600/431 |
| 2010/0049084 A1 * | 2/2010 | Nock | A61B 90/39 600/562 |
| 2010/0049085 A1 * | 2/2010 | Nock | A61B 90/39 600/562 |
| 2010/0152610 A1 | 6/2010 | Parihar et al. | |
| 2010/0160819 A1 | 6/2010 | Parihar et al. | |
| 2011/0071391 A1 * | 3/2011 | Speeg | A61M 5/427 600/431 |
| 2011/0071423 A1 * | 3/2011 | Speeg | A61B 90/92 600/562 |
| 2011/0071424 A1 * | 3/2011 | Nock | A61B 90/39 600/562 |
| 2011/0071431 A1 * | 3/2011 | Speeg | A61B 10/0275 600/567 |
| 2012/0330186 A1 | 12/2012 | Rhad et al. | |
| 2013/0053724 A1 | 2/2013 | Fiebig et al. | |
| 2013/0144188 A1 | 6/2013 | Fiebig et al. | |
| 2013/0324882 A1 | 12/2013 | Mescher | |
| 2014/0276037 A1 | 9/2014 | Johnson et al. | |

OTHER PUBLICATIONS

International Search Report and Written Opinion dated Jul. 5, 2016 for International Application No. PCT/US2016/030519, 11 pages.

\* cited by examiner

MARKER DELIVERY DEVICE FOR USE WITH MRI BREAST BIOPSY SYSTEM

This application is a National Stage Entry of PCT Application Ser. No. PCT/US16/30519, entitled "Marker Delivery Device for Use with MRI Breast Biopsy System," filed May 3, 2016, which claims priority to U.S. Provisional Application No. 62/157,604, entitled "Marker Delivery Device for Use with MRI Biopsy System," filed May 6, 2015.

FIELD OF THE INVENTION

The present invention relates generally to vacuum-assisted breast biopsy devices for use in breast biopsy procedures using MRI.

BACKGROUND

Biopsy samples have been obtained in a variety of ways in various medical procedures including open and percutaneous methods using a variety of devices. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device. Biopsy devices may be used under stereotactic guidance, ultrasound guidance, MRI guidance, Positron Emission Mammography ("PEM" guidance), Breast-Specific Gamma Imaging ("BSGI") guidance or otherwise.

The state of the art technology for conducting a breast biopsy is to use a vacuum-assisted breast biopsy device. A current textbook in this area is "Vacuum-Assisted Breast Biopsy with Mammotome®", available Nov. 11, 2012, copyright 2013 by Devicor Medical Germany Gumby, published in Germany by Springer Medicine Verilog, Authors: Markus Hahn, Anne Tardyon and Jan Cassel man, ISBN 978-3-642-34270-7, http://www.amazon.com/Vacuum-Assisted-Breast-Biopsy-Mammotome-Diagnostic/dp/36423-42701?ie=UTF8&keywords=vacuum%20assisted%20-breast%20biopsy%20with%20Mammotome&qid=14606-63723&ref_=sr_1_1&sr=8-1.

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Known biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 5,928,164, entitled "Apparatus for Automated Biopsy and Collection of Soft Tissue," issued Jul. 27, 1999; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,626,849, entitled "MRI Compatible Surgical Biopsy Device," issued Sep. 11, 2003; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,648,466, entitled "Manually Rotatable Piercer," issued Jan. 19, 2010; U.S. Pat. No. 7,837,632, entitled "Biopsy Device Tissue Port Adjustment," issued Nov. 23, 2010; U.S. Pat. No. 7,854,706, entitled "Clutch and Vaulving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatable Linked Thumbwheel and Tissue Sample Holder," issued Dec. 21, 2011; U.S. Pat. No. 8,118,755, entitled "Biopsy Sample Storage," issued Feb. 1, 2012; U.S. Pat. No. 8,206,316, entitled "Tether less Biopsy Device with Reusable Portion," issued on Jun. 26, 2012; U.S. Pat. No. 8,241,226, entitled "Biopsy Device with Rotatable Tissue Sample Holder," issued on Aug. 14, 2012; U.S. Pat. No. 8,251,916, entitled "Revolving Tissue Sample Holder for Biopsy Device," issued Aug. 28, 2012; U.S. Pat. No. 8,454,531, entitled "Icon-Based User Interface on Biopsy System Control Module," published May 21, 2009, issued on Jun. 4, 2013; U.S. Pat. No. 8,532,747, entitled "Biopsy Marker Delivery Device," issued Sep. 10, 2013; U.S. Pat. No. 8,702,623, entitled "Biopsy Device with Discrete Tissue Chambers," issued on Apr. 22, 2014; U.S. Pat. No. 8,764,680, entitled "Handheld Biopsy Device with Needle Firing," issued on Jun. 11, 2014; U.S. Pat. No. 8,801,742, entitled "Needle Assembly and Blade Assembly for Biopsy Device," issued Aug. 12, 2014; U.S. Pat. No. 8,858,465, entitled "Biopsy Device with Motorized Needle Firing," issued Oct. 14, 2014; U.S. Pat. No. 8,938,285, entitled "Access Chamber and Markers for Biopsy Device," issued Jan. 20, 2015; U.S. Pat. No. 9,095,326, entitled "Biopsy System with Vacuum Control Module," issued Aug. 4, 2015 and U.S. Pat. No. 9,095,326, entitled "Biopsy System with Vacuum Control Module," issued Aug. 4, 2015. The disclosure of each of the above-cited U.S. Patents is incorporated by reference herein.

Additional known biopsy devices and biopsy system components are disclosed in U.S. Pat. Pub. No. 2006/0074345, entitled "Biopsy Apparatus and Method," published Apr. 6, 2006 and now abandoned; U.S. Pat. Pub. No. 2008/0214955, entitled "Presentation of Biopsy Sample by Biopsy Device," published Sep. 4, 2008; U.S. Pat. Pub. No. 2009/0131821, entitled "Graphical User Interface for Biopsy System Control Module," published May 21, 2009, now abandoned; U.S. Pat. Pub. No. 2010/0152610, entitled "Hand Actuated Tether less Biopsy Device with Pistol Grip," published Jun. 17, 2010, now abandoned; U.S. Pat. Pub. No. 2010/0160819, entitled "Biopsy Device with Central Thumbwheel," published Jun. 24, 2010, now abandoned; U.S. Pat. Pub. No. 2013/0053724, entitled "Biopsy Device Tissue Sample Holder with Bulk Chamber and Pathology Chamber," published Feb. 28, 2013, will issue on May 3, 2016 as U.S. Pat. No. 9,326,755; U.S. Pat. Pub. No. 2013/0144188, entitled "Biopsy Device with Slide-In Probe," published Jun. 6, 2013; and U.S. Pat. Pub. No. 2013/0324882, entitled "Control for Biopsy Device," published Dec. 5, 2013. The disclosure of each of the above-cited U.S. Patent Application Publications, U.S. Non-Provisional Patent Applications, and U.S. Provisional Patent Applications is incorporated by reference herein.

A known localization mechanism used for guiding a core biopsy instrument is disclosed in U.S. Pat. No. 7,507,210, entitled "Biopsy Cannula Adjustable Depth Stop," issued Mar. 24, 2009, the disclosure of which is incorporated by reference herein. The localization mechanism includes a grid plate configured to removable receive a guide cube capable of supporting and orienting an MRI-compatible biopsy instrument. For instance, a combination of an obturator and targeting cannula/sleeve may be introduced through a breast to a biopsy site via the guide cube, with proper positioning confirmed using MRI imaging. The obturator may then be removed and the needle of a biopsy device may then be inserted through the targeting cannula/sleeve to reach the targeted lesion.

In U.S. Pat. Pub. No. 2005/0283069, entitled "MRI Biopsy Device Localization Fixture" published Dec. 22, 2005, the disclosure of which is incorporated by reference herein, a localization mechanism, or fixture, is described that is used in conjunction with a breast coil for breast compression and for guiding a core biopsy instrument during prone biopsy procedures in both open and closed Magnetic Resonance Imaging (MRI) machines. The localization fixture includes a three-dimensional Cartesian position able guide for supporting and orienting an MRI-compatible biopsy instrument, and, in particular, a cannula/sleeve to a biopsy site of suspicious tissues or lesions. Another merely illustrative localization mechanism used for guiding a core biopsy instrument is disclosed in U.S. Pat. No. 7,507,210, entitled "Biopsy Cannula Adjustable Depth Stop," issued Mar. 24, 2009, the disclosure of which is incorporated by reference herein. The localization mechanism includes a grid plate configured to removably receive a guide cube capable of supporting and orienting an MRI-compatible biopsy instrument. For instance, a combination of an obturator and targeting cannula/sleeve may be introduced through a breast to a biopsy site via the guide cube, with proper positioning confirmed using MRI imaging. The obturator may then be removed and the needle of a biopsy device may then be inserted through the targeting cannula/sleeve to reach the targeted lesion.

In U.S. Pat. No. 7,831,290, issued Oct. 20, 2010, the disclosure of which is incorporated by reference herein, a localization mechanism, or fixture, is described that is used in conjunction with a breast coil for breast compression and for guiding a core biopsy instrument during prone biopsy procedures in both open and closed Magnetic Resonance Imaging (MRI) machines. The localization fixture includes a three-dimensional Cartesian positionable guide for supporting and orienting an MRI-compatible biopsy instrument, and, in particular, a cannula/sleeve to a biopsy site of suspicious tissues or lesions.

A Z-stop may enhance accurate insertion, and prevent over-insertion or inadvertent retraction of a biopsy device targeting cannula/sleeve and obturator. In particular, a Z-stop may engage the localization fixture or cube at a distance from the patient set to restrict the depth of insertion of a biopsy device needle into a patient. Known Z-stop devices are disclosed in U.S. Pat. No. 7,507,210, entitled "Biopsy Cannula Adjustable Depth Stop," issued Mar. 24, 2009, the disclosure of which has been previously incorporated by reference herein.

The known current techniques of marking after a MRI Breast Biopsy is to insert the marker into the patient through the obturator, sleeve or biopsy device. None of the current, known techniques provide the ability to lock the orientation of the sleeve and marker adaptor together.

While several systems and methods have been made and used for obtaining a biopsy sample, it is believed that no one prior to the inventor has made or used the invention described in the appended claims.

SUMMARY OF THE INVENTION

The first aspect of the instant claimed invention is a biopsy system comprising: (a) a targeting set, wherein the targeting set includes a sleeve assembly; (b) a marker deployer, wherein the marker deployer comprises an elongate cannula, a plunger, and a handle, wherein the cannula extends distally from the handle and includes a lateral aperture, wherein at least a portion of the plunger is disposed within the cannula and is configured to selectively drive a marker through the lateral aperture of the cannula; and (c) an deployer adaptor, wherein the deployer adaptor is selectively attachable to the cannula of the marker deployer, wherein the deployer adaptor is operable to adapt the marker deployer for use with the sleeve assembly of the targeting set.

The second aspect of the instant claimed invention is a biopsy system comprising: (a) a targeting set, wherein the targeting set comprises a cannula, wherein the cannula includes a lumen; (b) a marker delivery device, wherein the marker delivery device comprises an outer cannula, and a handle, wherein at least a portion of the outer cannula is configured to deliver a marker to a biopsy site, wherein the outer cannula is configured for insertion through a needle of a biopsy device; (c) an adaptor device wherein the adaptor device comprises an elongate sheath and an attachment member, wherein the sheath is associated with the outer cannula of the marker delivery device, wherein the attachment member is associated with the handle of the marker delivery device, wherein the adaptor device is configured to be selectively attachable to the marker delivery device, wherein the outer cannula of the marker delivery device is configured for insertion into the cannula of the targeting set when the adaptor device is attached to the marker delivery device.

The third aspect of the instant claimed invention is a method for using a biopsy system comprising a targeting assembly including a sleeve assembly, a biopsy device, a marker delivery device, and an adaptor, wherein the method comprises: (a) introducing the sleeve assembly of the targeting assembly into tissue of a patient using an obturator inserted into the sleeve assembly; (b) removing the obturator from the sleeve assembly; (c) inserting at least a portion of the biopsy device into the sleeve assembly of the targeting assembly to collect a biopsy sample; (d) removing the biopsy device from the sleeve assembly of the targeting assembly after collecting a biopsy sample; (e) attaching the adaptor to at least a portion of the marker delivery device; (f) inserting the marker delivery device and with the adaptor attached thereto into the sleeve assembly of the targeting assembly; and (g) using the marker delivery device to deploy a marker into tissue of a patient.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

Figure 1:
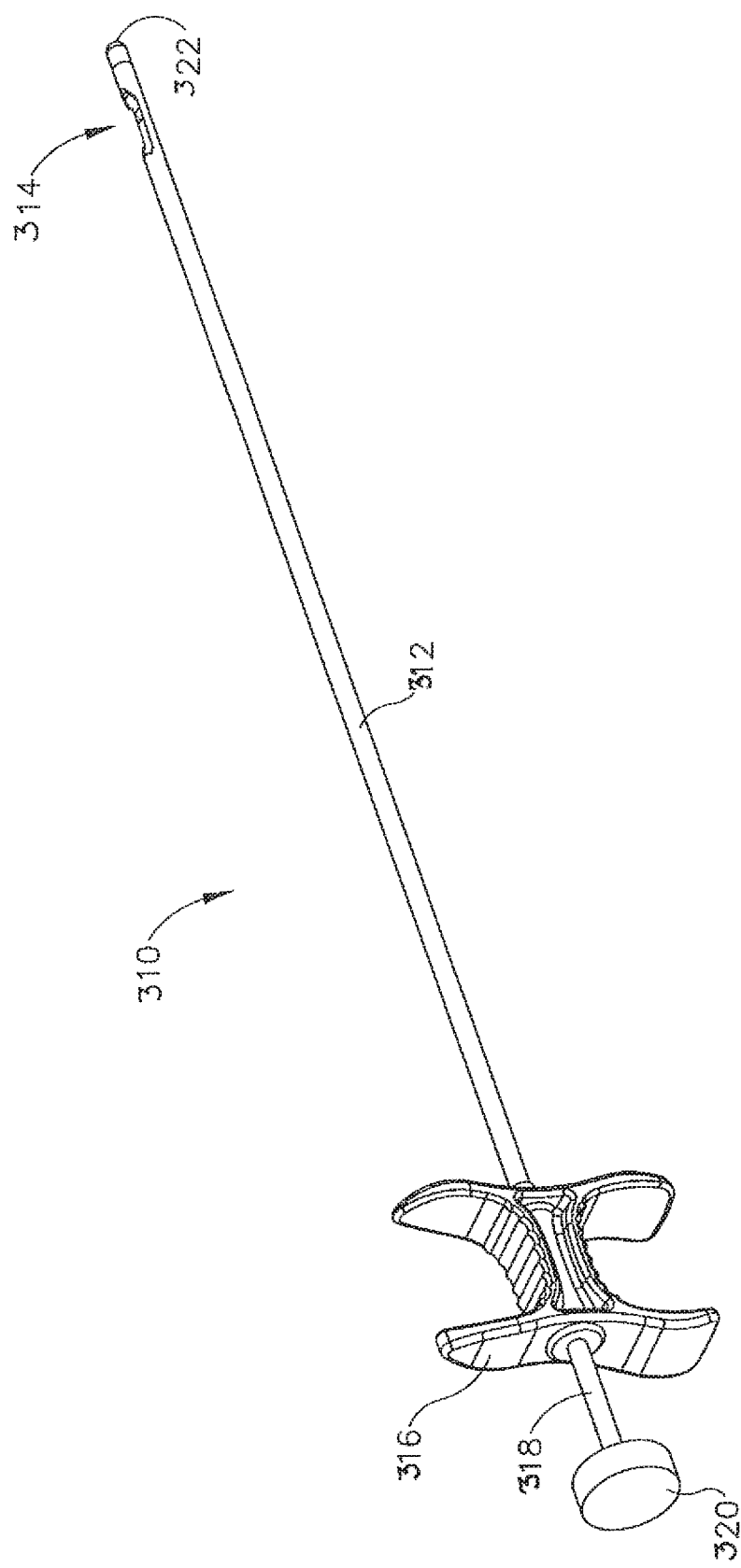
FIG. 1 depicts a perspective view of an exemplary marker delivery device for use with the biopsy system of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

The marker adaptor for the MRI breast biopsy device provides the operator with the ability to easily mark after an MRI biopsy procedure through the biopsy sleeve. The flexible shaft marker of the instant claimed invention snaps into the marking adaptor which creates the oval shape that mates with the inner surface of the sleeve. This locks the orientation of the sleeve and marker, with adaptor, together. The marker adaptor of the instant claimed invention also contains a hard-stop which allows the user to place the biopsy marker in the correct location.

The marker adaptor contains an oval profile to lock orientation to the inside of the sleeve. It also contains snap features which locate on the marker handle. The hard-stop surface allows the marker to be placed inside of the breast at the correct Z-depth. The marker retention ribs keep the body of the marker contained within the marker adaptor.

FIGS. 1, 2, 3, 4, 5, 6, 7, 8 and 9 of U.S. Pat. No. 7,507,210, incorporated by reference in its entirety, depict a perspective view of a biopsy system including a control module remotely coupled to a biopsy device, and including a localization fixture with a lateral grid plate used in conjunction with a rotatable cube to position an obturator or a probe of the biopsy device to a desired insertion depth as set by a ring stop.

During the breast biopsy procedure, typically the patient's breasts hang pendulously respectively into breast apertures on the examination table. For convenience, herein a convention is used for locating a suspicious lesion by Cartesian coordinates within breast tissue referenced to localization fixture and to thereafter selectively position an instrument, such as needle of probe that is engaged to holster portion to form biopsy device.

To enhance hands-off use of biopsy system, especially for repeated re-imaging within the narrow confines of a closed bore MRI machine, biopsy system may also guide obturator encompassed by cannula. Depth of insertion is controlled by a depth stop device longitudinally positioned on either needle or cannula. Alternatively, depth of insertion may be controlled in any other suitable fashion.

In typical MRI breast biopsy procedures, a targeting set comprising cannula and obturator is associated with a probe. In particular the obturator is slid into cannula and the combination is guided through guide cube to the biopsy site within the breast tissue. Obturator is then withdrawn from cannula, then the needle of the probe is inserted in cannula, and then biopsy device is operated to acquire one or more tissue samples from the breast via needle.

FIG. 1 illustrates a marker delivery device (310) which includes an elongate outer cannula (312) having a marker exit, such as side opening (314) formed adjacent to, but spaced proximally from, the distal end of the cannula (312).

A grip (316) can be provided at the proximal end of cannula (312). A push rod (318) is provided, with push rod (318) extending coaxially in cannula (312) such that push rod (318) is configured to translate within cannula (312) to displace one or more markers through side opening (314) (see FIG. 2). Rod (318) may have sufficient rigidity in compression to push a marker from an internal lumen (315) of cannula (312) out through opening (314), yet be relatively flexible in bending. A plunger (320) is coupled at the proximal end of rod (318) for forcing rod (318) distally in cannula (312) to deploy a marker out of cannula (312).

A user may grasp grip (316) with two fingers, and may push on plunger (320) using the thumb on the same hand, so that marker delivery device (310) is operated by a user's single hand. A spring (not shown) or other feature may be provided about rod (318) to bias rod (318) proximally relative to grip (316) and cannula (312).

Figure 2:
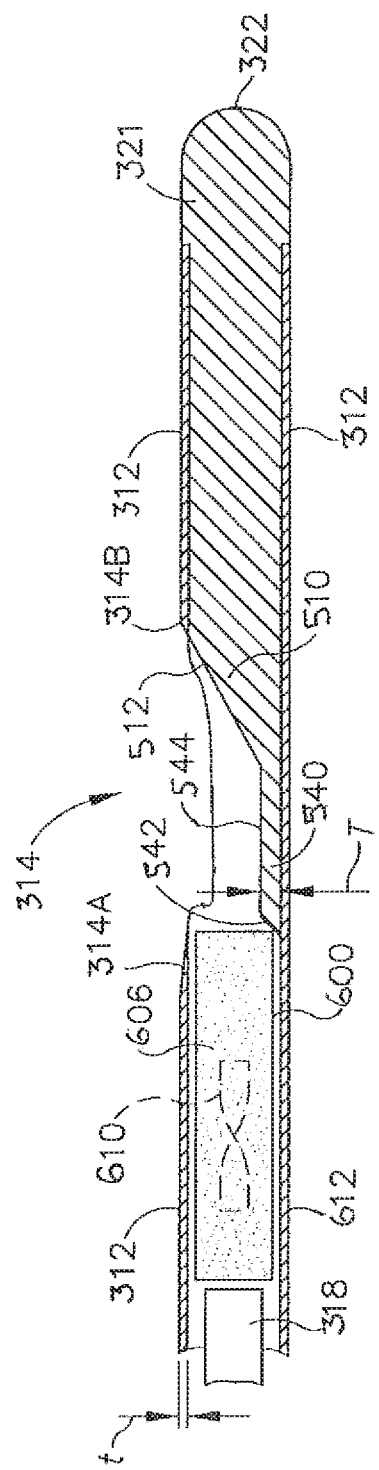
FIG. 2 depicts a front cross-sectional view of a distal portion of the marker delivery device of FIG. 1.

FIG. 2 depicts a cross-sectional view of a distal portion of the marker delivery device (310). FIG. 2 shows a biopsy marker (600) disposed in internal lumen (315) of cannula (312). In the present example, marker (600) comprise a biodegradable or otherwise resorbable body (606), such as a generally cylindrically shaped body of collagen, and a metallic, generally radiopaque marker element (610) (shown in phantom) disposed within or otherwise carried by body (606).

Cannula (312) may be formed of any suitable metallic or non-metallic material. In some versions, cannula (312) is formed of a thin walled hollow tube formed of a suitable medical grade MRI compatible plastic or polymer. One suitable material is a thermoplastic elastomer, such as Polyether block amide (PEBA), such as is known under the tradename PEBAX. PEBAX polymers are available from Arkema. See http://www.pebax.com/en/Cannula (312) may be formed of PEBAX, and may be substantially transparent to visible light and X-ray.

Side opening (314) may be formed by cutting away a portion of the wall of cannula (312). Side opening (314) communicates with an internal lumen (315) of cannula (312). Side opening (314) may extend axially (in a direction parallel to the axis of lumen (315)) from a proximal opening end (314A) to a distal opening end (314B), as illustrated in FIG. 2.

In the present example, distal tip (322) extends from the distal end of cannula (312) and is rounded as shown in FIG. 2. Referring to FIG. 2, the distal end of cannula (312) is closed by a unitary endpiece (321), with a portion of endpiece (321) extending into internal lumen (315) of cannula (312). Endpiece (321) may be a molded or cast component. Endpiece (321) comprises a tip (322), a ramp (510) having a ramp surface (512), and a marker engaging element (540). Ramp surface (512) aids in directing marker (600) from internal lumen (315) through side opening (314). Marker engaging element (540) helps to retain marker (600) in internal lumen (315) until the user intends to deploy marker (600).

Marker engaging element (540) is disposed within internal lumen (315), and at least a portion of marker engaging element (540) is disposed distally of proximal end (314A) of side opening (314). Marker engaging element (540) extends along a portion of the floor of cannula (312) under opening (314) such that marker engaging element (540) is positioned to reinforce the portion of cannula (312) in which opening (314) is formed. For instance, by positioning marker engaging element (540) underneath opening (314), as shown in FIG. 2, element (540) helps to stiffen cannula (312) in the region where wall of cannula (312) is cut to form opening (314). As shown in FIG. 2, marker engaging element (540) extends from the proximal most portion of ramp surface (512), and does not extend proximally of side opening (314), though in other embodiments, a portion of element (540) may extend proximally of opening (314).

As shown in FIG. 2, marker engaging element (540) is in the form of a step having a generally uniform thickness (T) along element's (540) axial length, except that element (540) has a tapered proximal end (542). Tapered proximal end (542) forms an included angle with the longitudinal axis of lumen (315) (included angle with a horizontal line in FIG. 2) of about 45 degrees, while ramp surface (512) forms an included angle with the longitudinal axis of about 30 degrees. Of course, any number of other suitable angles may be used. Thickness (T) may be greater than wall thickness (t) of cannula (312). In some versions, thickness (T) is at least about twice thickness (t). For instance, thickness (T) may be between about 0.018 inch to about 0.040 inch, and wall thickness (t) may be between about 0.13 mm (0.005 inches) to about 0.2 mm (0.008 inches). The internal diameter of lumen (15) may be about 3.05 mm (0.120 inches). Of course, any number of other suitable thicknesses and diameters may be used.

As shown in FIG. 2, an upwardly facing surface (544) (surface facing opening (314)) of marker engaging element (540) extends distally to contact ramp surface (512), so that there is not a space or gap between surface (544) and ramp surface (512). Such an arrangement is advantageous to reduce the possibility that marker (600), upon moving past marker engaging element (540), may become lodged between marker engagement element (540) and ramp (512). In some versions, marker engaging element (540), ramp (510), and/or tip (322) are formed of, or include, a material that is relatively more radiopaque than the wall of cannula (312). For instance, where element (540), ramp (510), and tip (322) are formed as an integral endpiece (321), endpiece (321) may include a radiopaque additive, such as barium sulfate. For instance, endpiece (321) may be a component molded of PEBAX, with about 20 percent by weight barium sulfate added to the molten PEBAX mold composition. The relatively more radiopaque marker engaging element (540), ramp (510), and tip (322) may be useful in distinguishing the position of those components using radiographic imaging. Also, where ramp (510) and/or step of engaging element (540) are positioned in association with opening (314), the addition of a radiopaque material can help identify the position of opening (314), and the position of marker (600) relative to opening (314) before, during, or after deployment of marker (600).

Only one marker (600) is shown disposed in lumen (315) in the figures. However, it should be understood that multiple markers (600) may be disposed in marker delivery device (310), such as in an end to end configuration. Markers (600) may have the same size and shape, or alternatively have different sizes and/or shapes.

Cannula (612) may be generally transparent to visible light and x-ray, and endpiece (321) may be generally opaque to visible light and x-ray. It may be desirable to color endpiece (321) with a dye or other suitable colorant in the liquid mold composition. For instance, it may be desirable to have different size markers (600) (e.g. length and/or diameter) for different biopsy procedures. For instance, it may be desirable to provide a larger marker (600) if a relatively large biopsy sample is taken, and a smaller marker (600) if a relatively small biopsy sample is taken. Endpiece (321) may be colored using one of multiple colors to indicate the size of marker (600) disposed in cannula (312). For instance, if three marker (600) sizes are provided, endpiece (321) may be colored one of three colors to identify which of marker (600) sizes are disposed in cannula (312) of a marker device (310). Endpiece (321) may also be colored to indicate a particular size (diameter or length) biopsy needle with which marker delivery device (310) is to be used. Additionally, multiple marker delivery devices (310) could be packaged in kit form, with the kit including marker delivery devices (310) having different size markers (600) and correspondingly colored endpieces (321).

Figure 3:
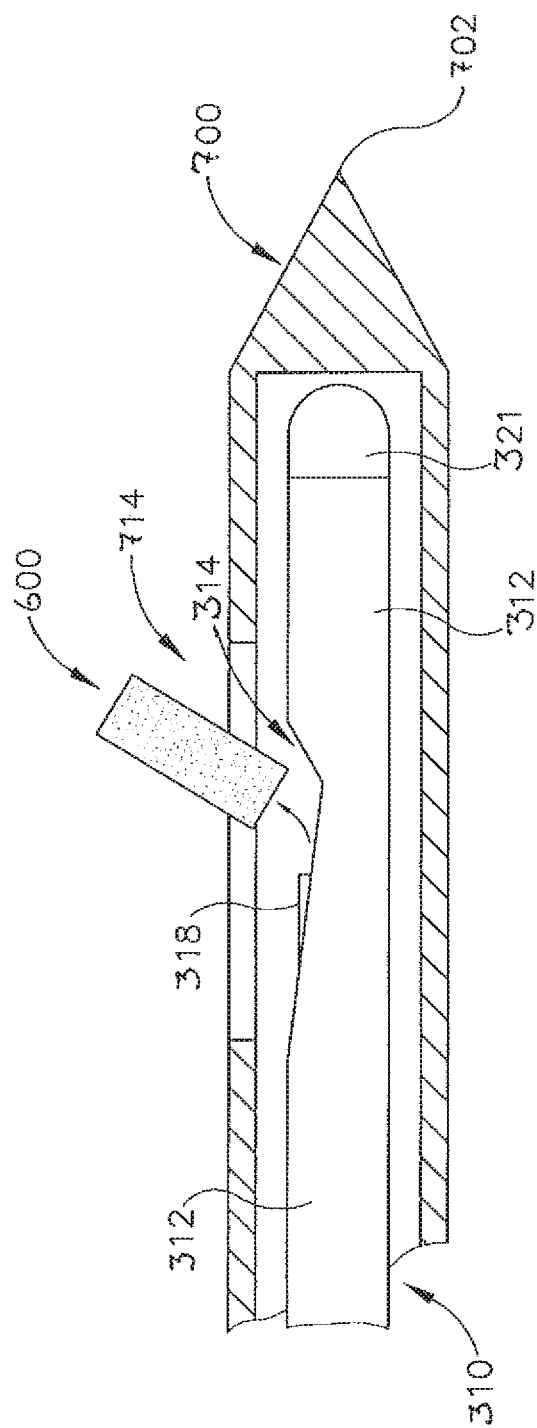
FIG. 3 depicts a front cross-sectional view of a marker being deployed from the distal portion of the marker delivery device of FIG. 1 and through a lateral tissue receiving port in a biopsy needle to mark a biopsy site.

Referring to FIG. 3, marker delivery device (310) is used to deploy a marker (600) to mark a biopsy location within a patient. In FIG. 3, a cannular biopsy needle (700), similar to needle (90) of probe (91) described above, is shown having a closed distal end with piercing tip (702) and a lateral tissue receiving aperture (714). Marker deployer (310) is introduced to a biopsy site through biopsy needle (700), which may be the same needle (700) used to collect a tissue sample from the biopsy site as described above with respect to the biopsy device as described in U.S. Pat. No. 7,507,210. In addition to or in alternative, biopsy needle (700) may be of the type used with single insertion, multiple sample vacuum assisted biopsy devices. Several such biopsy devices are disclosed in the various patents and patent applications that have been referred to and incorporated by reference herein, though other biopsy devices may be used.

FIG. 3 shows the distal end of marker deployer (310) disposed within needle (700). Needle (700) may be positioned in tissue, and a biopsy sample may be obtained through opening (714), thereby providing a biopsy cavity adjacent opening (714). Then, after the tissue sample has been obtained and transferred proximally through needle (700), and without removing needle (700) from the patient's tissue, deployer (310) is inserted into a proximal opening in needle (700). In FIG. 3, needle (700) and deployer (310) are positioned such that opening (314) of cannula (312) and opening (714) of needle (700) are substantially aligned axially and circumferentially. Then, with deployer (310) and needle (700) so positioned at the biopsy site, push rod (318) is advanced to deploy marker (600) up ramp surface (512), through opening (314), and then through opening (714), into the biopsy cavity.

In some instances, distal opening end (314B) may not align with ramped surface (512) due to inadvertent errors during manufacturing and/or assembly of marker delivery device (310). Accordingly, a marker (600) may become caught on distal opening end (314B) when marker (600) is deployed from device (310). It may therefore be desirable to include a second ramped feature on endpiece (321) to allow smooth deployment of marker (600) from device (310) even if ramped surface (512) and distal opening end (314B) are misaligned, as will be seen below.

Figure 4:
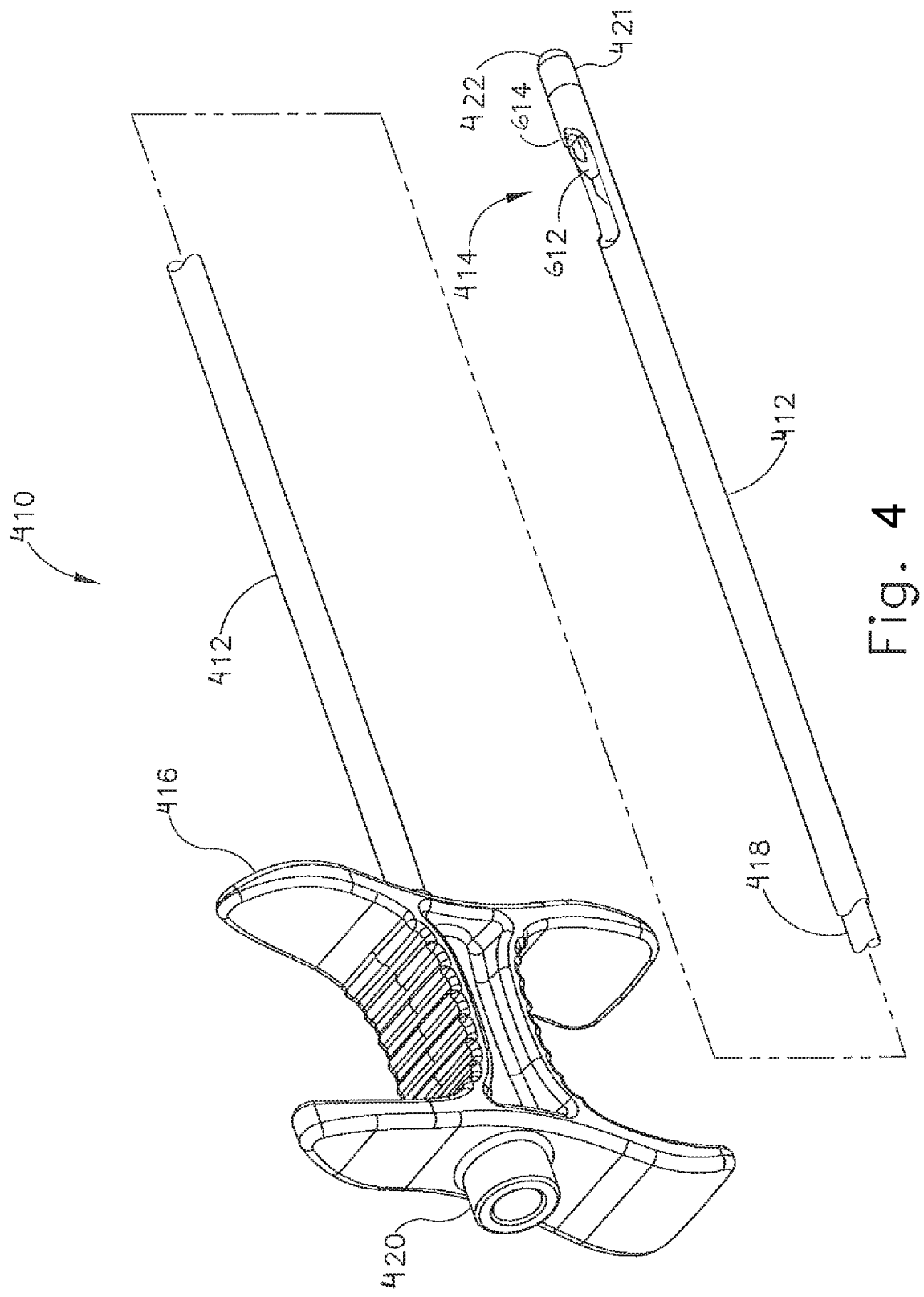
FIG. 4 depicts a perspective view of another exemplary marker delivery device for use with the biopsy system of FIG. 1.
Figure 5:
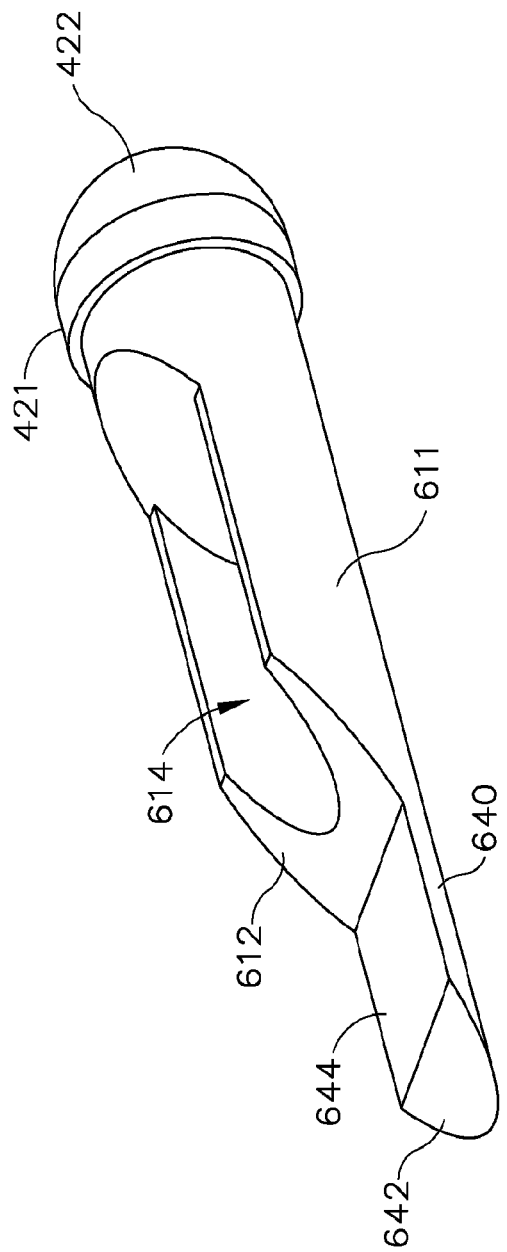
FIG. 5 depicts a perspective view of an endpiece of the marker delivery device of FIG. 4.

FIG. 4 shows another exemplary marker delivery device (410) that is similar to marker delivery device (310), except that marker delivery device (410) comprises a compound ramped endpiece (421). Like marker deliver device (310), marker delivery device (410) comprises a cannula (412), a side opening (414), a grip (416), a plunger (420), and an endpiece (421). As shown in FIG. 5, endpiece (421) is similar to endpiece (321) in that endpiece (421) comprises a ramp (611), and a rounded distal tip (422). Marker engaging element (440) and tip (422) are similar to and tip (322). Ramp (611) is similar to ramp (510), except that ramp (611) comprises a first ramped surface (612) and a rod receiving channel (614) disposed in first ramped surface (612). It should be understood that rod receiving channel (614) is configured such that marker (600) will travel over rod receiving channel along first ramped surface (612); yet rod receiving channel (614) will receive rod (418).

Figure 6:
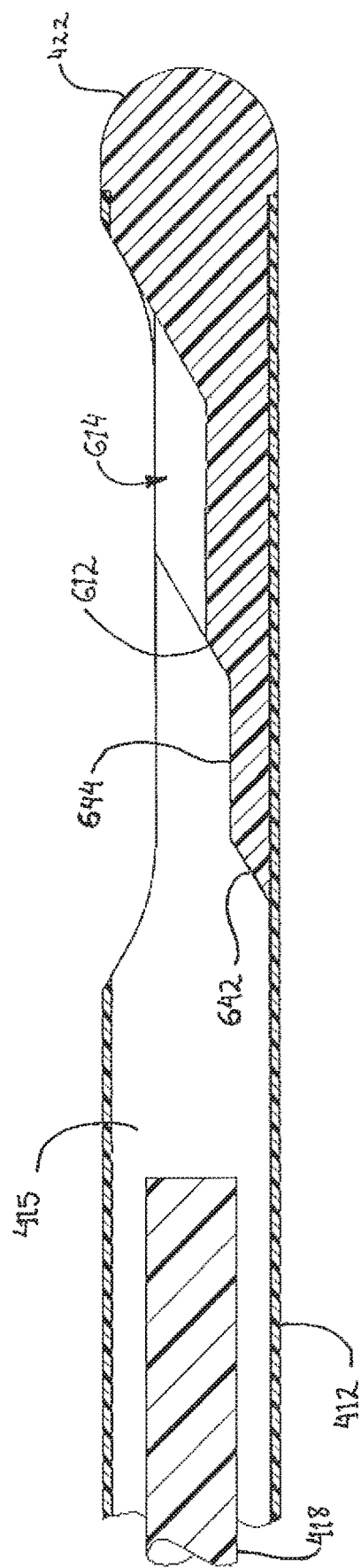
FIG. 6 depicts a front cross-sectional view of a distal portion of the marker delivery device of FIG. 4.
Figure 7:
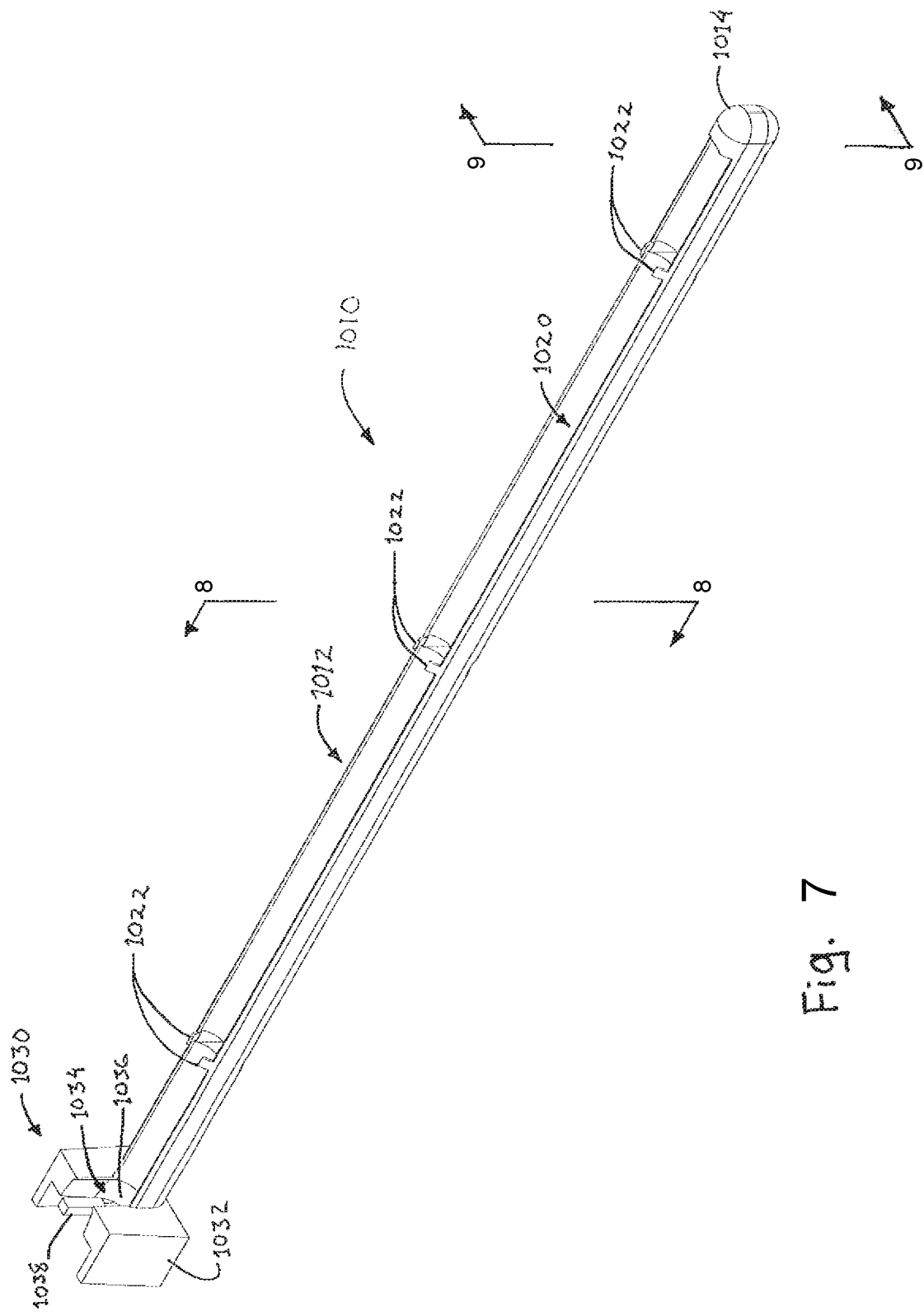
FIG. 7 depicts a perspective view of an exemplary adaptor device for use with the marker delivery devices of FIGS. 1 and 4.

FIG. 6 shows endpiece (421) coupled with cannula (412), such that a portion of endpiece (421) is inserted within a distal portion of cannula (412). Marker engaging element (640) is adjacent to side opening (414) of cannula (412). A tapered proximal end (642) of marker engaging element (640) forms an included angle with the longitudinal axis of lumen (415) of about 45 degrees. First ramped surface (612) forms an included angle with the longitudinal axis of lumen (415) of about 30 degrees. Of course, any number of other suitable angles may be used. A distal opening end (414B) of opening (414) is formed at substantially the same angle as first ramped surface (612) such that first ramped surface (612) and distal opening end (414B) of cannula (412) form a substantially flush surface when endpiece (421) is inserted within cannula (412).

Marker delivery device (410) may be used to deploy a marker (600) to mark a biopsy location within a patient. For instance, marker delivery device (410) may introduced to a biopsy site through a biopsy needle (700), which may be the same needle (700) used to collect a tissue sample from the biopsy site. Needle (700) may be positioned in tissue, and a biopsy sample may be obtained through opening (714), thereby providing a biopsy cavity adjacent opening (714). Then, after the tissue sample has been obtained and transferred proximally through needle (700), and without removing needle (700) from the patient's tissue, marker delivery device (410) is inserted into a proximal opening in needle (700). Needle (700) and marker delivery device (410) are positioned such that opening (414) of cannula (412) and opening (714) of needle (700) are substantially aligned axially and circumferentially. A marker (600) is positioned within lumen (415) of cannula (412) proximal to marker engaging element (640) such that marker engaging element (640) holds marker (600) within cannula (412). Then, with deployer (410) and needle (700) so positioned at the biopsy site, a push rod (418) is advanced to deploy marker (600). As push rod (418) advances marker (600), marker (600) cammingly slides along ramped proximal end (642) of marker engaging element (640), along an upwardly facing surface (644) and up first ramped surface (612) over rod receiving channel (614). Marker (600) is then deployed through opening (414), and then through opening (714) of needle (700), into the biopsy cavity.

Although marker delivery devices (310, 410) are described above as being insertable into a needle of a probe, it should be understood that in some instances it may be desirable to use such marker delivery devices (310, 410) in connection with other instruments and/or devices associated with a biopsy procedure. For instance, in one merely exemplary use of marker delivery device (310, 410) it may be desirable to insert marker delivery device (310, 410) into a cannula similar to cannula described above. However, in such examples the cannula may not consist of a geometry suitable for use with marker delivery device (310, 410). By way of example only, the cannula may be of a generally ovular construction while marker delivery device (310, 410) includes an outer cannula (312, 412) of a round construction. Accordingly, in such examples it may be desirable to equip marker delivery device (310, 410) with an additional device or devices to make marker delivery device (310, 410) readily useable with the cannula. Various examples of how marker delivery device (310, 410) may be adapted for use with a cannula similar to cannula will be described in greater detail below; while other examples will be apparent to those of ordinary skill in the art according to the teachings herein.

FIGS. 7-10 show an adaptor device (1010) for use with marker delivery devices (310, 410) described above. As will be described in greater detail below, adaptor device (1010) is generally selectively attachable to outer cannula (312, 412) of marker delivery device (310, 410) to adapt marker delivery device (310, 410) for insertion into a cannula (1110) similar to cannula described in. Adaptor device (1010) comprises an elongate sheath (1012) and an attachment member (1030). Adaptor device (1010) is generally of unitary construction, comprising a single MRI compatible material such as plastic or polymer. One suitable material is a thermoplastic elastomer, such as Polyether block amide (PEBA), such as is sold by Arkema under the tradename PEBAX.

Elongate sheath (1012) extends distally from attachment member (1030) terminating in a rounded distal tip (1014). Between attachment member (1030) and distal tip (1014), elongate sheath (1012) defines a cannula channel (1020) that is configured to receive outer cannula (312, 412) of marker delivery device (310, 410).

Figure 8:
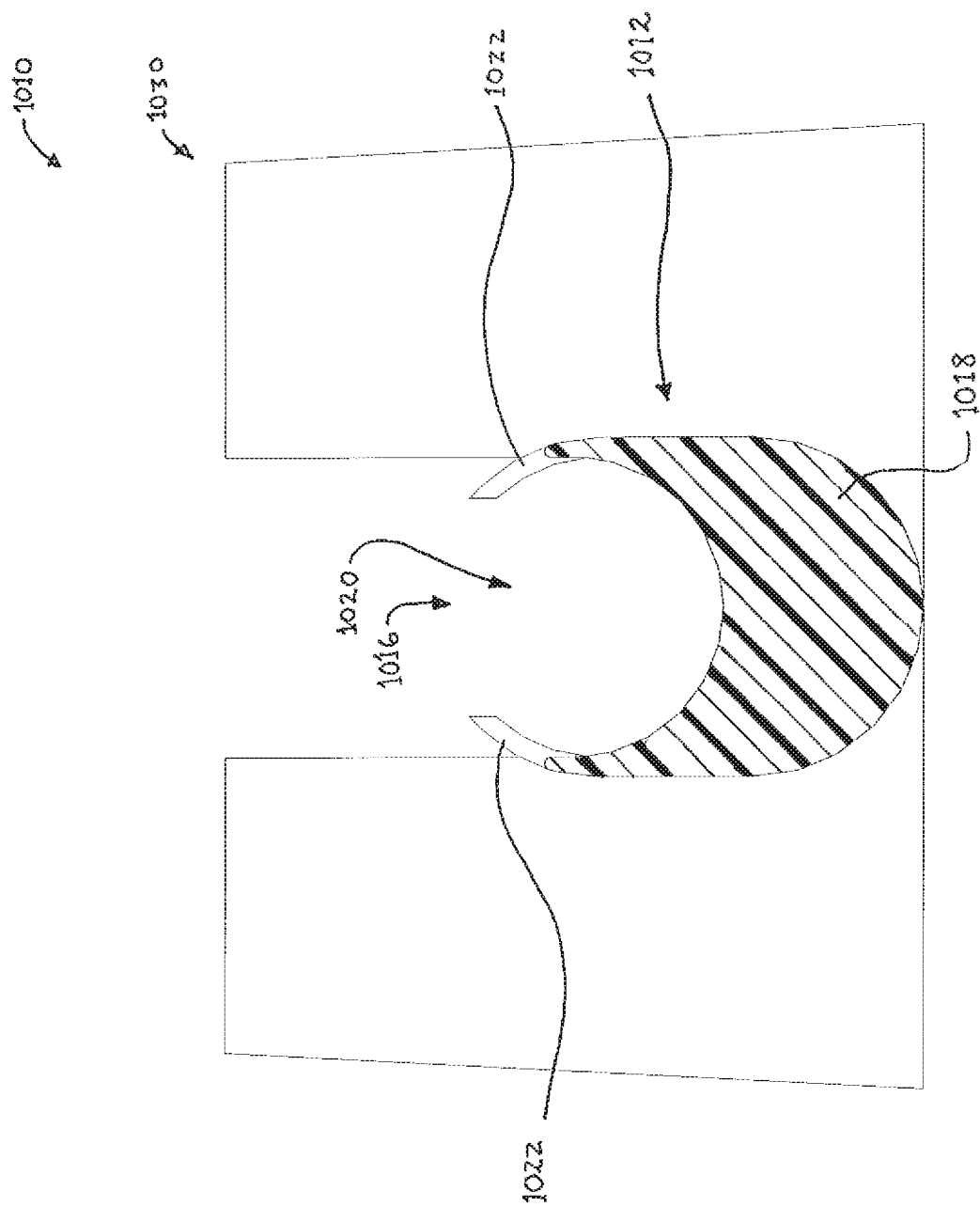
FIG. 8 depicts a side cross-sectional view of the adaptor device of FIG. 7, with the cross-section taken along line 8-8 of FIG. 7.
Figure 19:
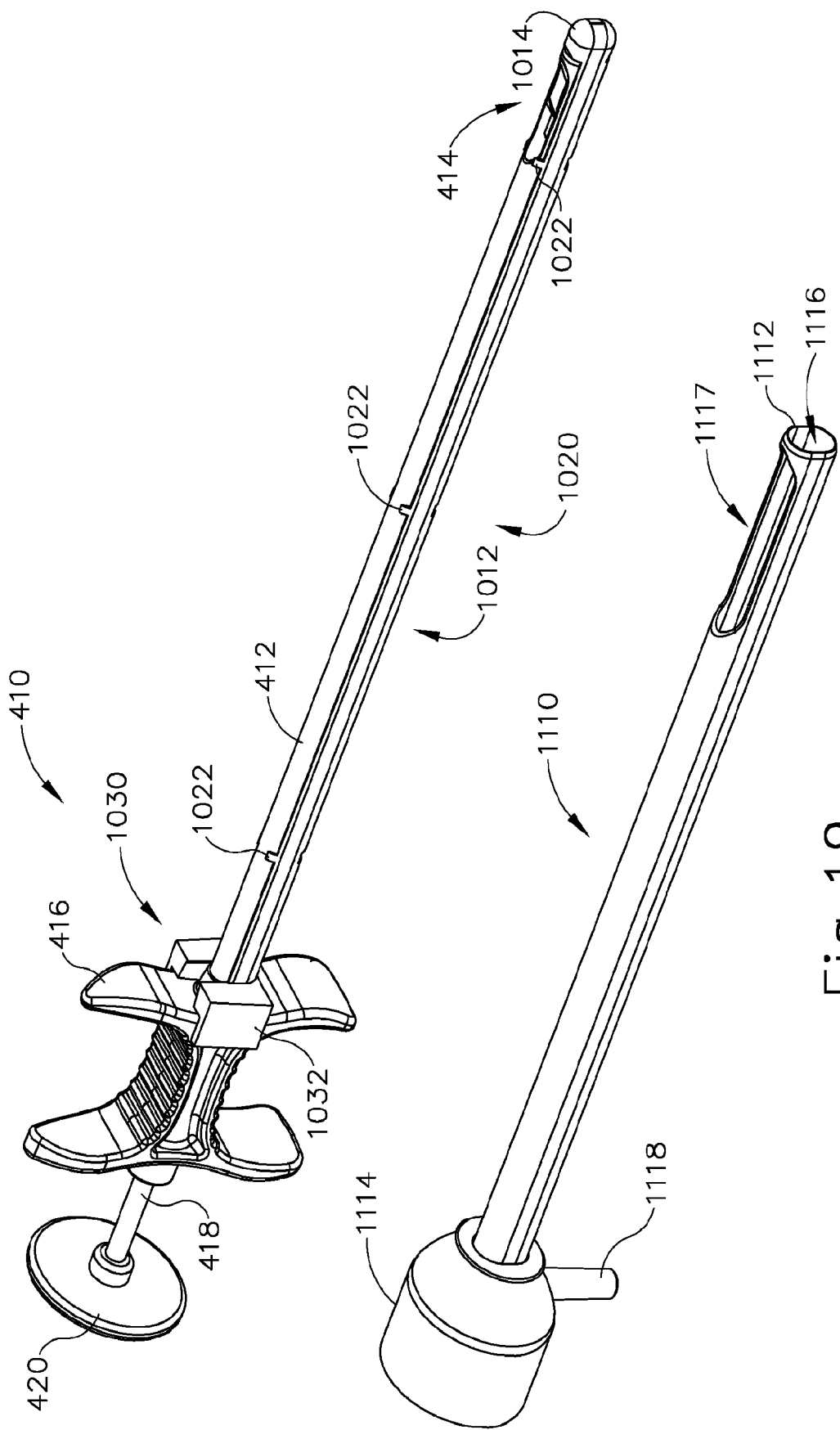
FIG. 19 depicts perspective view of another exemplary cannula adjacent to the marker delivery device of FIG. 4 and the adaptor device of FIG. 7.

As can best be seen in FIG. 8, elongate sheath (1012) has a generally ovular shape with an open top portion (1016) and a thick bottom portion (1018). As will be described in greater detail below, the particular shape of elongate sheath (1012) is configured such that when elongate sheath (1012) is attached to cannula (312, 412) of marker delivery device (310, 410), the combination defines a solid transverse ovular cross-section that may occupy a corresponding lumen of cannula (1110) (as can be seen in FIG. 19). Open top portion (1016) is in communication with cannula channel (1020) and is sized to receive cannula (1110).

Returning to FIG. 7, elongate sheath (1012) further includes a plurality of retaining arms (1022) extending into open top portion (1016). Retaining arms (1022) are of integral construction with elongate sheath (1012). Thus, retaining arms (1022) comprise the same plastic or polymer material as elongate sheath (1012). Because of this it should be understood that retaining arms (1022) are resilient in nature such that retaining arms (1022) are deformable to permit insertion of cannula (1110); yet selectively retain cannula (1110) within cannula channel (1020) once cannula (1110) is inserted. In other examples, retaining arms (1022) may have similar properties but may comprise a separate material and are fixedly secured to elongate sheath (1012).

Elongate sheath (1012) of the present example comprises three pairs of retaining arms (1022) spaced equidistantly along the length of elongate sheath (1012). It should be understood that although three pairs of retaining arms (1022) are shown, any suitable number of retaining arms (1022) may be used. Moreover, while retaining arms (1022) are shown as being grouped in adjacent pairs, it should be understood that in other examples retaining arms (1022) may alternatively be staggered on each side of elongate sheath (1012). Of course, any other suitable configuration of retailing arms (1022) may be used as will be apparent to those of ordinary skill in the art in view of the teachings herein.

Figure 9:
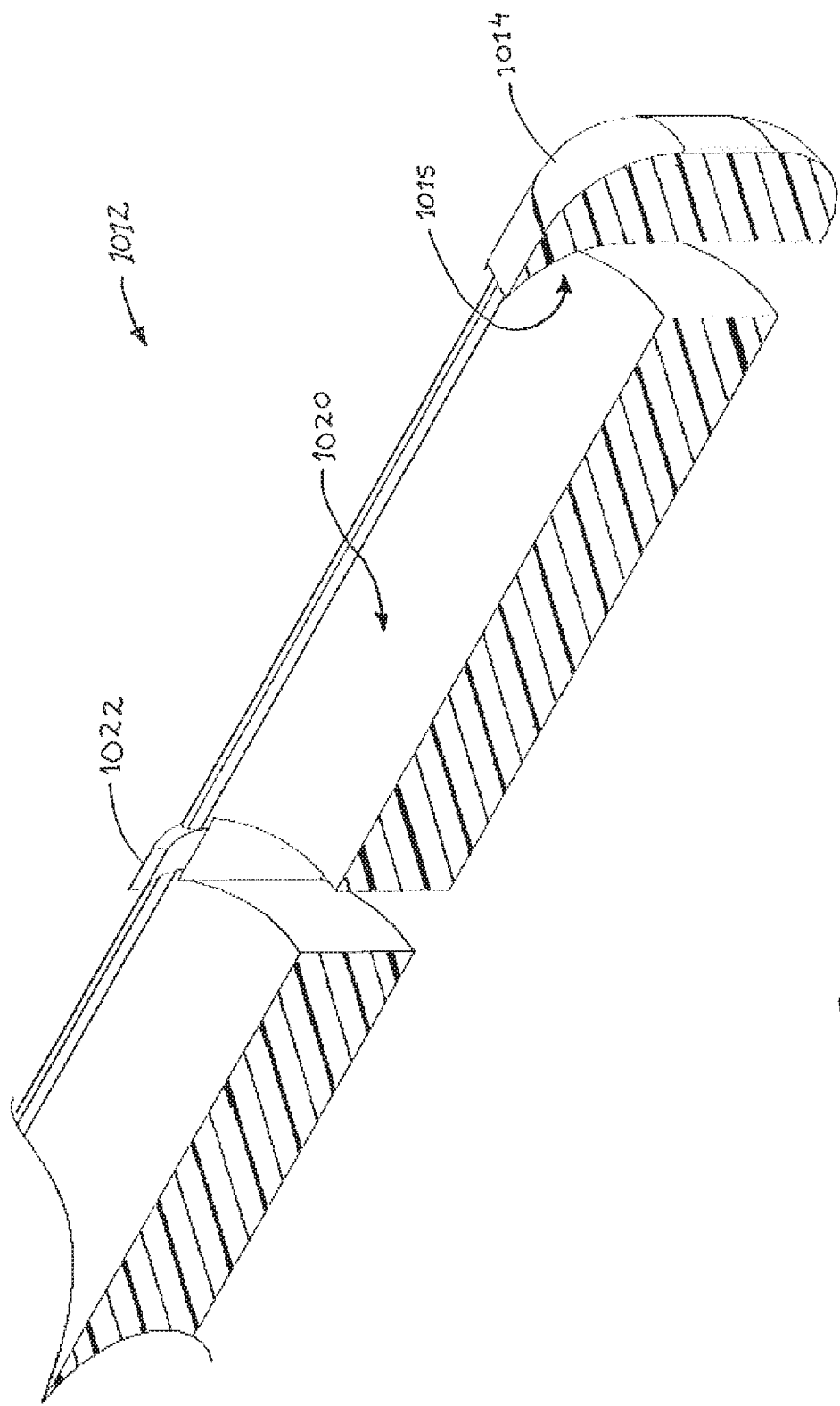
FIG. 9 depicts a partial perspective cross-sectional view of the adaptor device of FIG. 7, with the cross-section taken along line 9-9 of FIG. 7.

FIG. 9 shows distal tip (1014) in greater detail. In particular, as can be seen the exterior of distal tip (1014) is generally rounded. The interior of distal tip (1014) defines an internal cavity (1015). Internal cavity (1015) is configured to receive at least a portion of cannula (1110) such that cannula (1110) may be at least partially held within cannula channel (1020) by internal cavity (1015). While distal tip (1014) of the present example is shown as comprising internal cavity (1015), it should be understood that in other examples internal cavity (1015) may be enlarged, reduced in size, or simply omitted.

Figure 10:
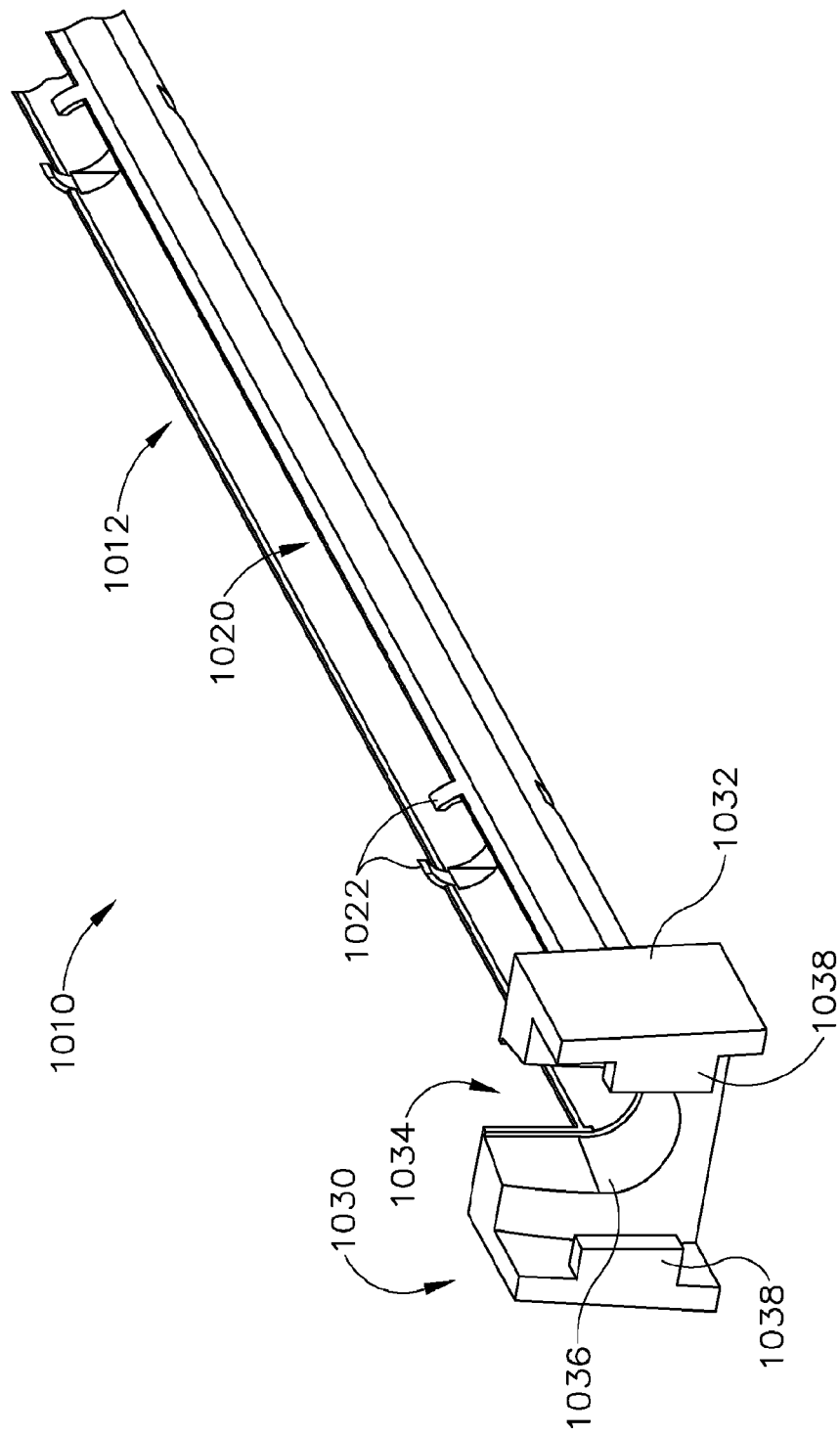
FIG. 10 depicts a partial perspective view of a proximal portion of the adaptor device of FIG. 7.
Figure 11:
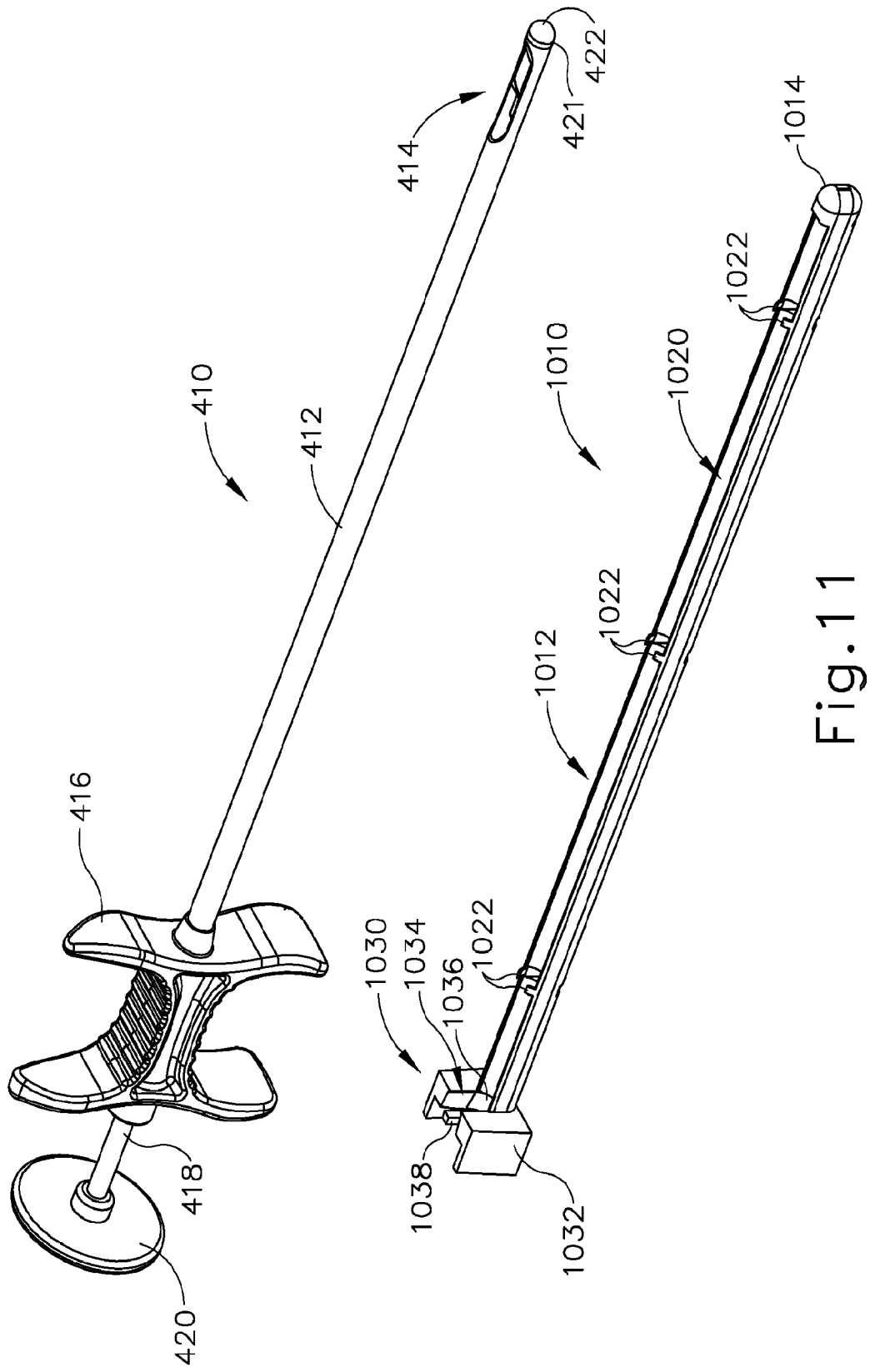
FIG. 11 depicts a perspective view of the marker delivery device of FIG. 4 and the adaptor device of FIG. 7, with the marker delivery device and adaptor device in a separated state.

FIG. 10 shows attachment member (1030) in greater detail. As can be seen, attachment member (1030) comprises a body (1032) and two lock tabs (1038). Body (1032) is adjacent to elongate sheath (1012) and is of integral construction therewith. Body (1032) includes an opening (1034) disposed in alignment with cannula channel (1020) of elongate sheath (1012). As will be understood, opening (1034) is configured to receive cannula (1110) such that cannula may pass through body (1032) and into cannula channel (1020). Body (1032) further includes a chamfered surface (1036) surrounding opening (1034). It should be understood that chamfered surface (1036) is merely optional and may be omitted in some examples.

Each lock tab (1038) is positioned on an opposite side of attachment member (1030). In particular, lock tabs (1038) are of integral construction with body (1032) and protrude laterally inwardly toward each other. As will be described in greater detail below, lock tabs (1038) are generally configured to resiliently engage against at least a portion of marker delivery device (310, 410) to secure outer cannula (312, 412) of marker delivery device (310, 410) within cannula channel (1020) of sheath (1012). Like with retaining arms (1022) described above, lock tabs (1038) are configured to be resilient in nature, yet deformable such that at least a portion of marker delivery device (310, 410) may be received by lock tabs (1038) and then resiliently held in place.

Although not shown, it should be understood that attachment member (1030) may include other features related to attachment of marker delivery device (310, 410). For instance, in some examples attachment member (1030) further includes snap features that are configured to provide an operator with tactile or auditory feedback indicating when attachment member (1030) is engaged with marker delivery device (310, 410). Such features may be desirable because tactile or audible feedback may enhance the usability of attachment member (1030).

FIGS. 11-18 show an exemplary operation of attaching adaptor device (1010) to marker delivery device (410). It should be understood that although adaptor device (1010) is described herein as being used in conjunction with marker delivery device (410), adaptor device (1010) may also be used in conjunction with marker delivery device (310) or any other suitable marker delivery device as will be apparent to those of ordinary skill in the art in view of the teachings herein. As can best be seen in FIGS. 11 and 13, adaptor device (1010) and marker delivery device (410) initially begin separated from one another.

Figure 12:
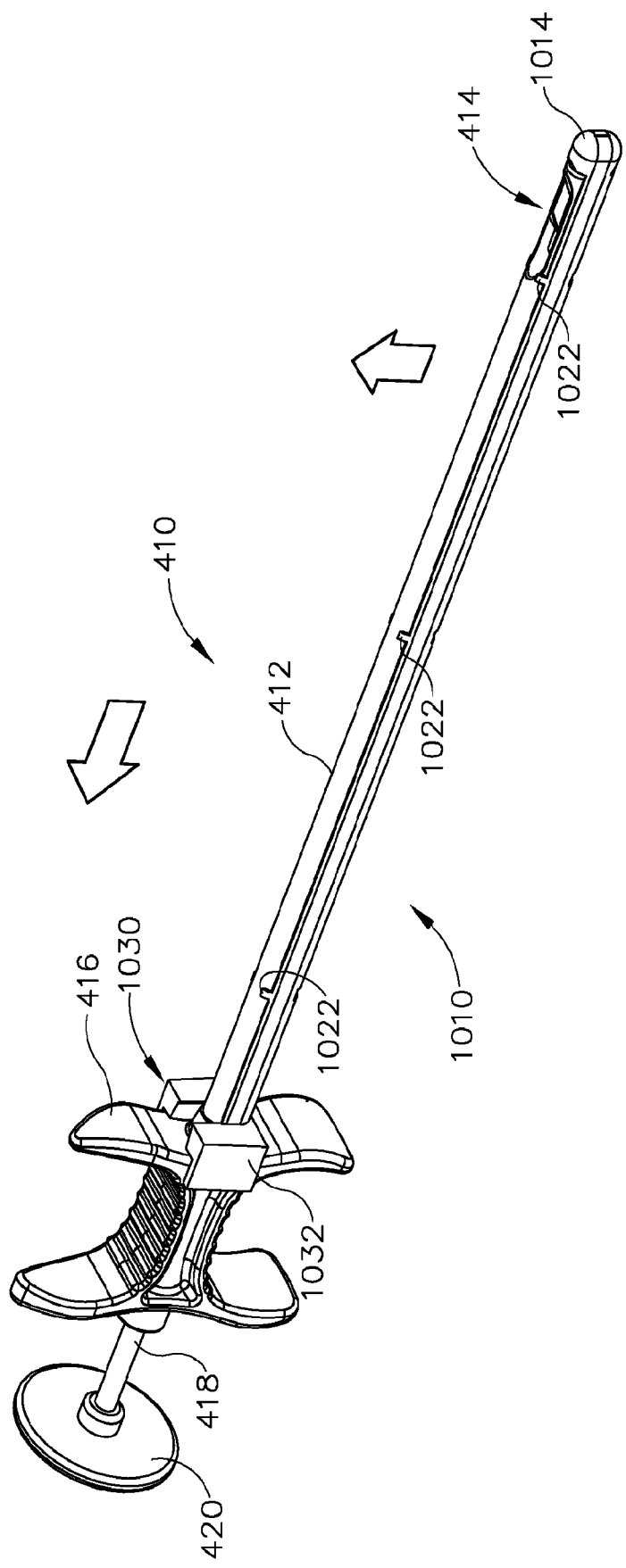
FIG. 12 depicts a perspective view of the marker delivery device of FIG. 4 and the adaptor device of FIG. 7, with the adaptor device attached to the marker delivery device.
Figure 13:
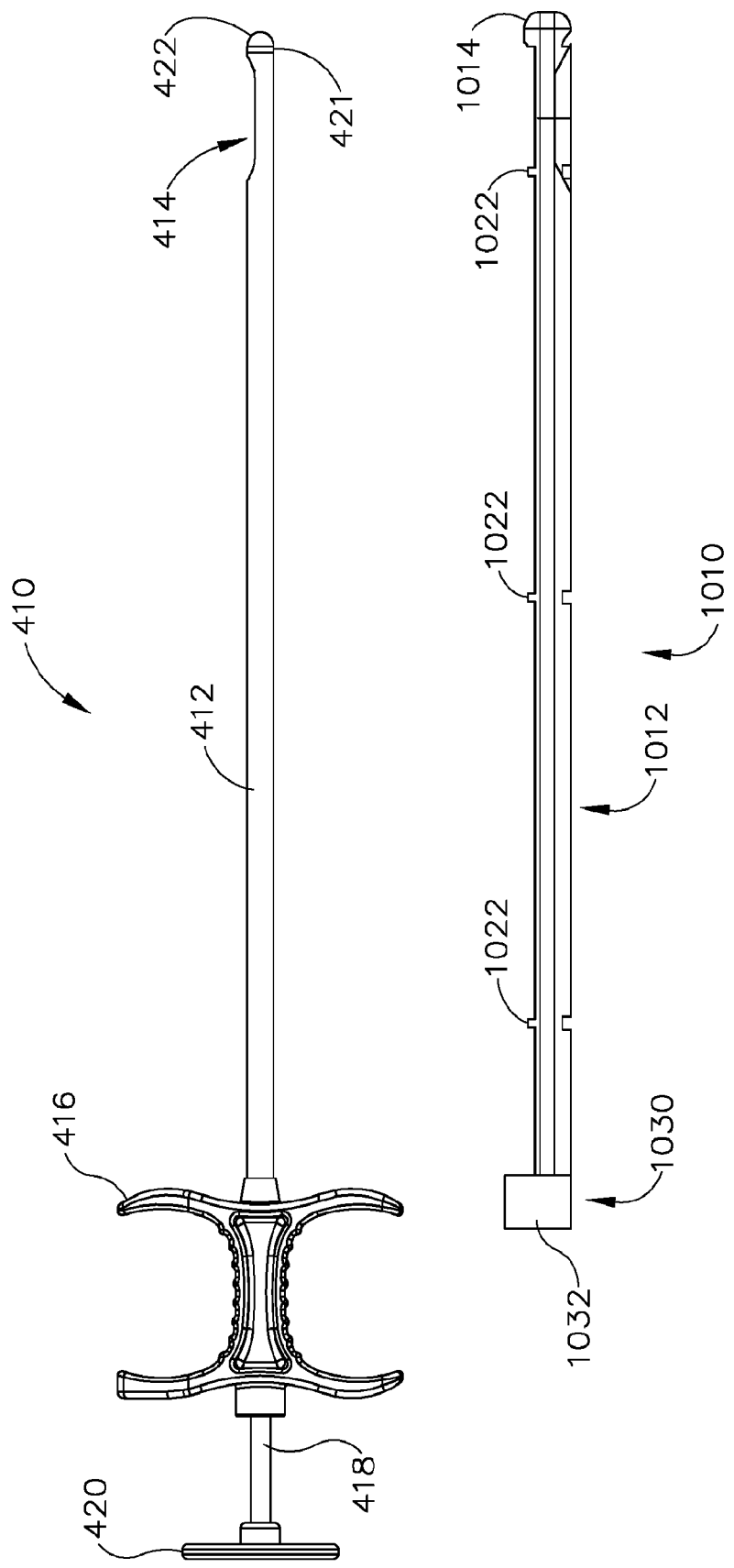
FIG. 13 depicts a front elevational view of the marker delivery device of FIG. 4 and the adaptor device of FIG. 7, with the marker delivery device and the adaptor device in the separated state.
Figure 14:
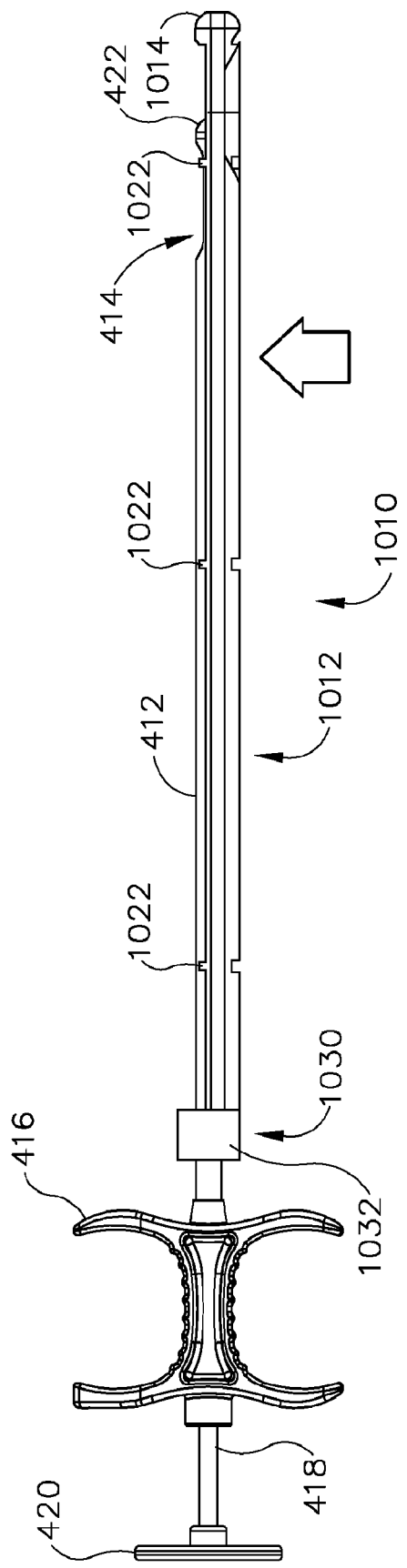
FIG. 14 depicts a front elevational view of the marker delivery device of FIG. 4 and the adaptor device of FIG. 7, with the adaptor device partially attached to the marker delivery device.

To attach adaptor device (1010) to marker delivery device (410), a user may generally gasp adaptor device (1010) and move adaptor device (1010) upwardly and longitudinally relative to marker delivery device (410) as indicated in FIG. 12. In particular, as can best be seen in FIGS. 14 and 16, adaptor device (1010) is initially moved upwardly relative to marker delivery device (410) such that outer cannula (412) of marker delivery device (410) is inserted into cannula channel (1020) of adaptor device (1010). As outer cannula (412) enters cannula channel (1020), retaining arms (1022) of adaptor device (1010) are temporarily displaced by outer cannula (412) until retaining arms (1022) return to their initial shape in a position that surrounds at least a portion of the outer diameter of outer cannula (412). It should be understood that as adaptor device (1010) is moved upwardly, attachment member (1030) of adaptor device (1010) is disposed distally of grip (416) of marker delivery device (410). Although attachment member (1030) is shown as being disposed a particular distance from grip (416), attachment member (1030) may be disposed from grip (416) any suitable distance as will be apparent to those of ordinary skill in the art in view of the teachings herein.

Figure 15:
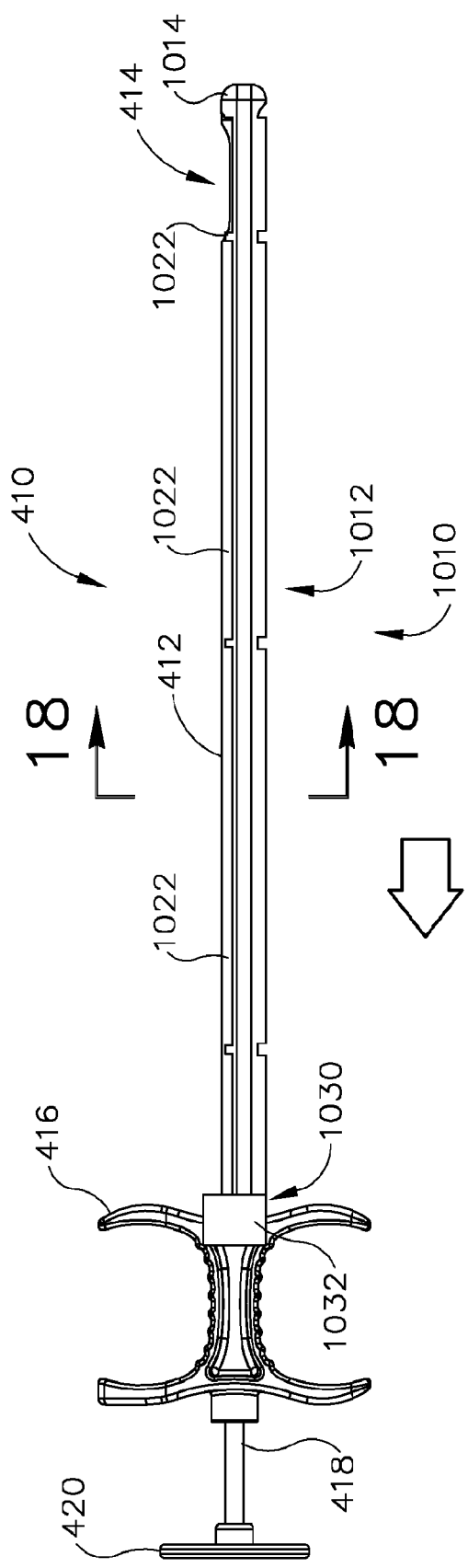
FIG. 15 depicts a front elevational view of the marker delivery device of FIG. 4 and the adaptor device of FIG. 7, with the adaptor device fully attached to the marker delivery device.
Figure 16:
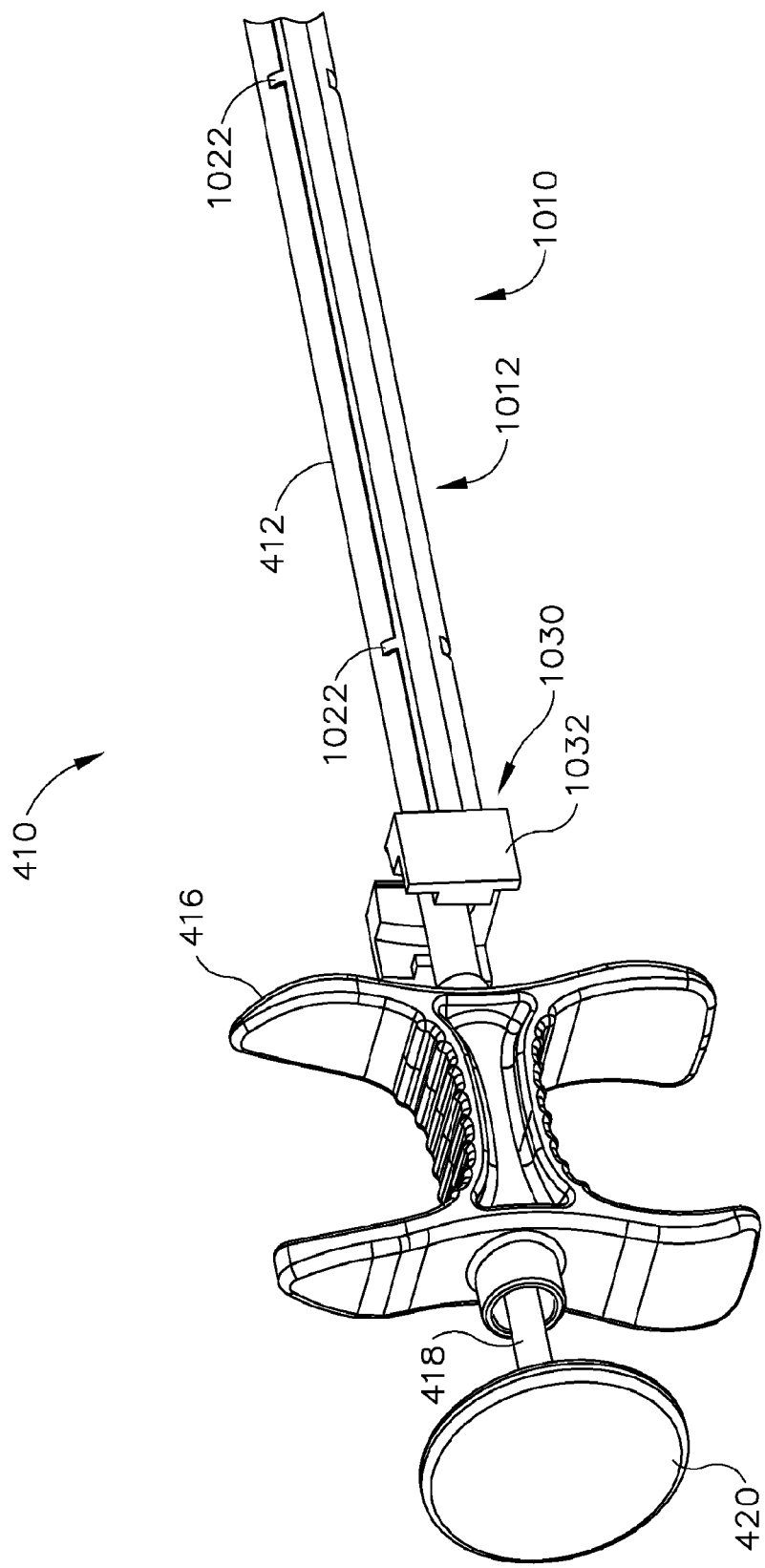
FIG. 16 depicts a partial perspective view of the marker delivery device of FIG. 4 and the adaptor device of FIG. 7, with the adaptor device partially attached to the marker delivery device.
Figure 17:
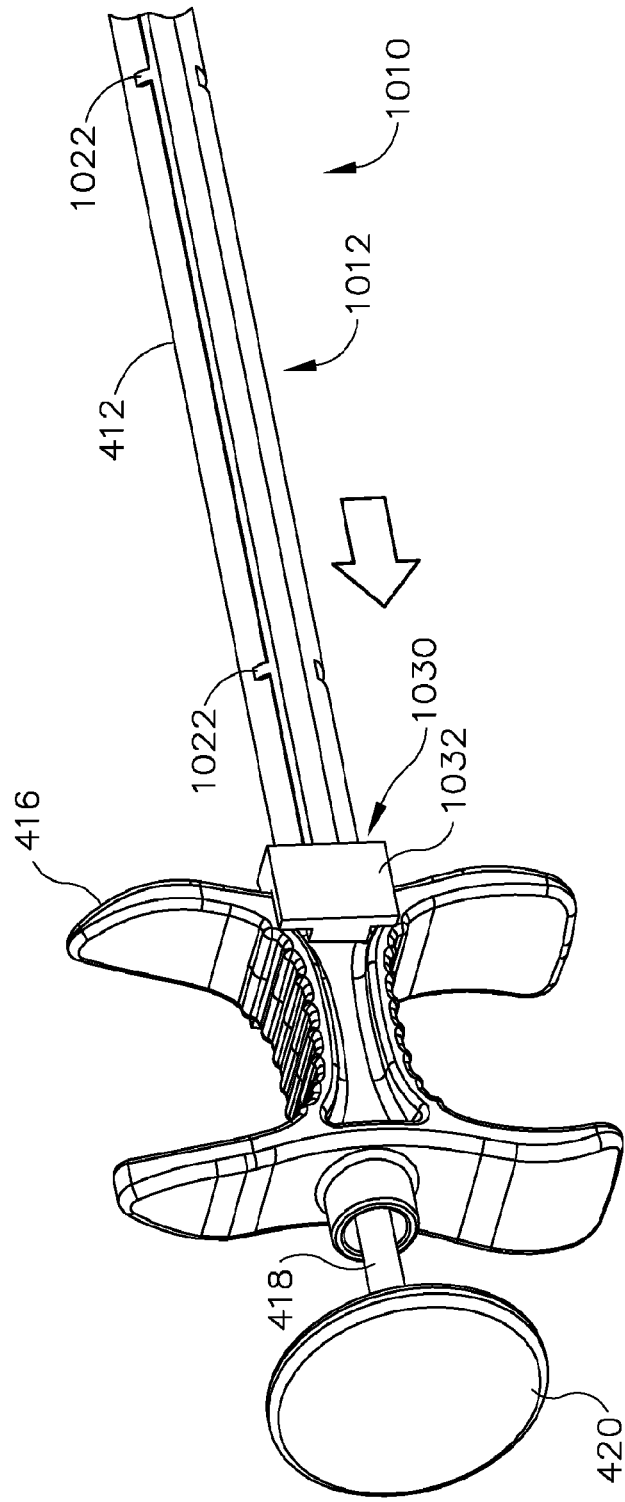
FIG. 17 depicts a partial perspective view of the marker delivery device of FIG. 4 and the adaptor device of FIG. 7, with the adaptor device fully attached to the marker delivery device.

As can be seen in FIG. 15, an operator may next drive adaptor device (1010) proximally to engage attachment member (1030) with grip (416) of marker delivery device (410). Additionally, proximal movement of adaptor device (1010) causes distal tip (422) of marker delivery device (410) to enter internal cavity (1015) in distal tip (1014) of adaptor device (1010). As can be seen in FIG. 17, driving adaptor device (1010) proximally causes each lock tab (1038) of attachment member (1030) to engage with features of grip (416) thereby attaching attachment member (1030) to grip (416). In particular, grip (416) temporarily deflects each lock tab (1038) away from grip (416) as attachment member (1030) moves proximally until each lock tab (1038) clears the features of grip (416). Once each lock tab (1038) has cleared the features of grip (416), each lock tab (1038) returns to its initial position, thereby selectively securing attachment member (1030) to grip (416).

Figure 18:
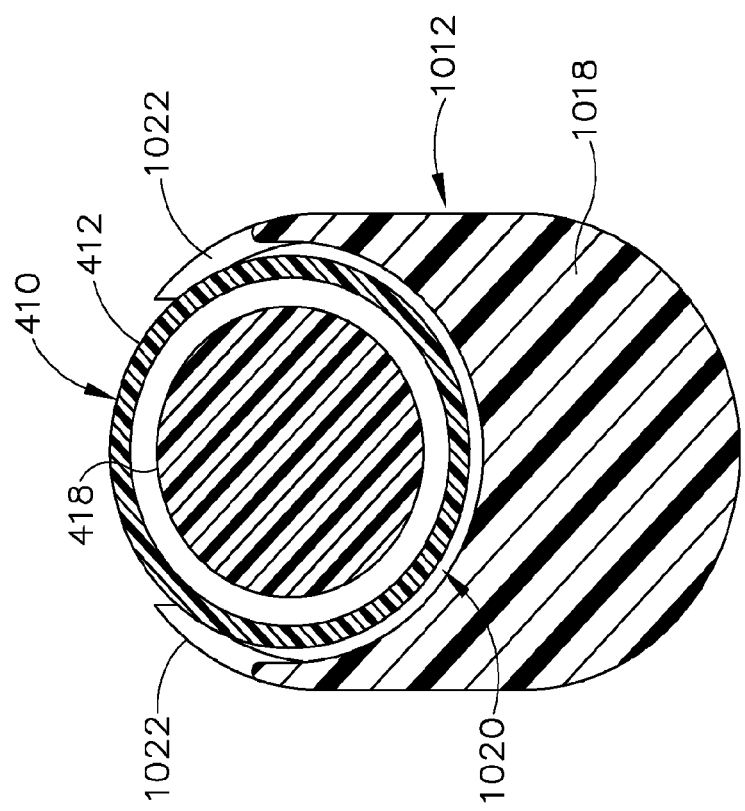
FIG. 18 depicts a side cross-sectional view of the adaptor device of FIG. 7 fully attached to the marker delivery device of FIG. 4, with the cross-section taken along line 18-18 of FIG. 15.

FIG. 18 shows a cross-section of the final positioning of adaptor device (1010) inserted onto marker delivery device (410). As can be seen, the outer surface of outer cannula (412) of marker delivery device (410) is held in position within cannula channel (1020) by retaining arms (1022). The combination of outer cannula (412) and elongate sheath (1012) defines a generally complete ovular cross-section. As will be described in greater detail below, such a cross-section corresponds to an internal shape of cannula (1110).

Once adaptor device (1010) is attached to marker delivery device (410), marker delivery device (410) is configured for use with cannula (1110). FIG. 19 shows marker delivery device (410) with adaptor device (1010) attached and cannula (1110). Cannula (1110) of the present example is substantially the same as cannula (94) described above unless otherwise noted herein. For instance, cannula (1110) of the present example extends distally from a hub (1114) and defines a lumen (1116). Cannula (1110) includes an open distal end (1112) and a lateral aperture (1117) disposed proximally of open distal end (1112). Hub (1414) includes attachment features (not shown) and a port (1118). The attachment features may be used to couple hub (1114) to a portion of an obturator (not shown) or other devices or features associated with an MRI biopsy targeting set. Port (1118) is in communication with lumen (1116) defined by cannula (1110). Port (1118) may be optionally coupled to a fluid source for delivery of therapeutic substances, saline, or other fluids to a biopsy site via lumen (1116). It should be understood that port (1118) is merely optional and may be omitted in some examples. While not shown, it should be understood that hub (1114) includes other features and/or components such as seals, thumbwheels, fluid channels, and/or additional lumen similar to cylindrical hub (198) described above.

As described above, with adaptor device (1010) attached to marker delivery device (410) an operator may insert marker delivery device (410) into cannula (1110). It should be understood that during a biopsy procedure, cannula (1110) may be inserted into tissue of a patient during insertion of marker delivery device (410). Moreover, it should be understood that prior to insertion of marker delivery device (410), cannula (1110) may be used for a variety of other purposes. By way of example only, cannula (1110) may first be used in conjunction with an obturator similar to obturator (92) described above to pierce tissue and locate cannula (1110) adjacent to a biopsy site. Next, the obturator may be removed and a biopsy device similar to biopsy device (14) described above may be inserted into cannula (1110) to extract a biopsy sample from the patient. Once biopsy sampling is complete, the biopsy device may be removed from cannula (1110) and marker delivery device (410) may be inserted into cannula (1110) for marking a biopsy site as described below. Of course, cannula (1110), marker delivery device (410), and adaptor device (1010) may be used during at any other suitable point in a biopsy procedure as will be apparent to those of ordinary skill in the art in view of the teachings herein.

Figure 20:
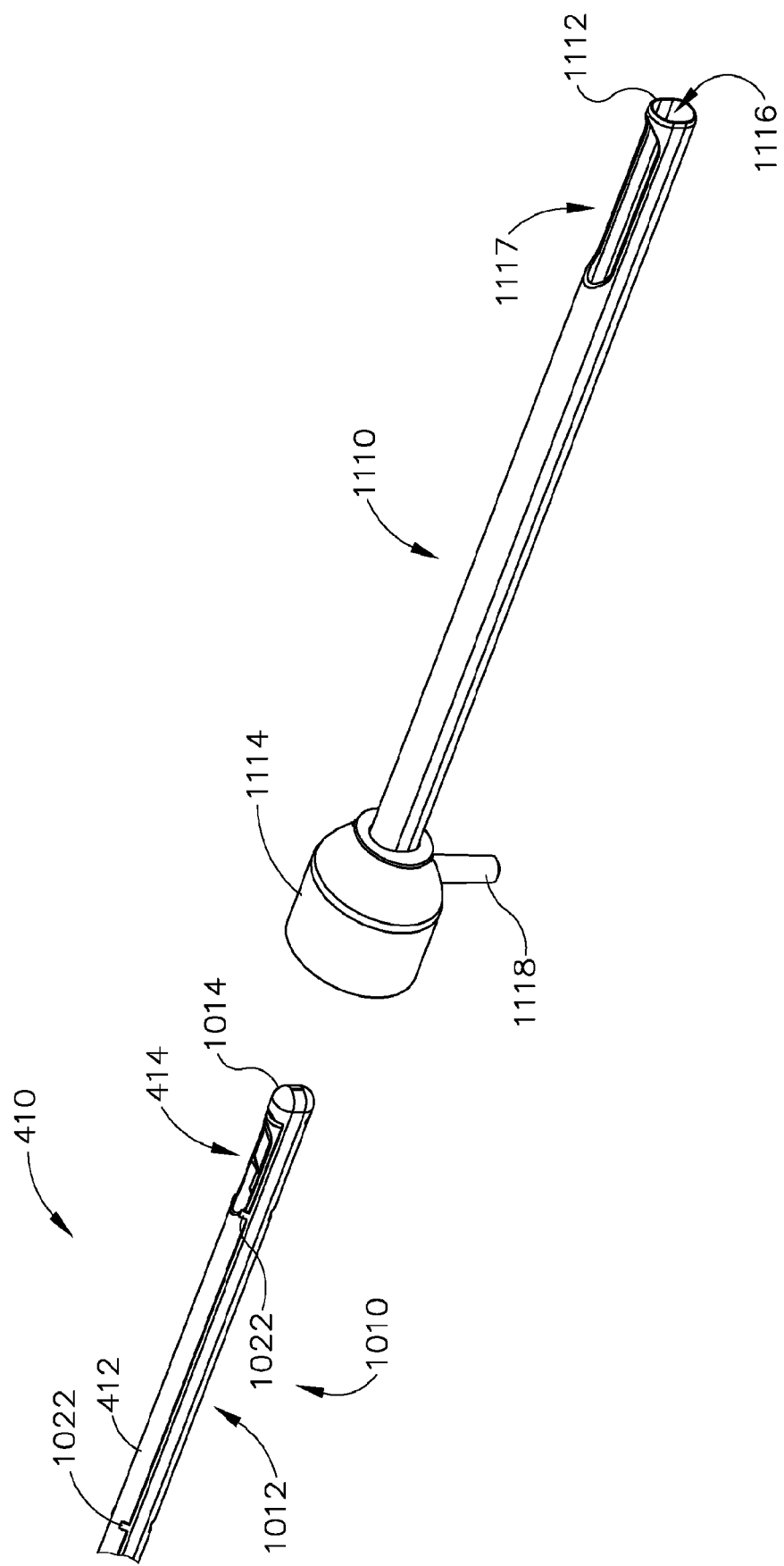
FIG. 20 depicts a perspective view of the cannula of FIG. 19, with the marker delivery device of FIG. 4 and the adaptor device of FIG. 7 adjacent to a hub of the cannula.
Figure 21:
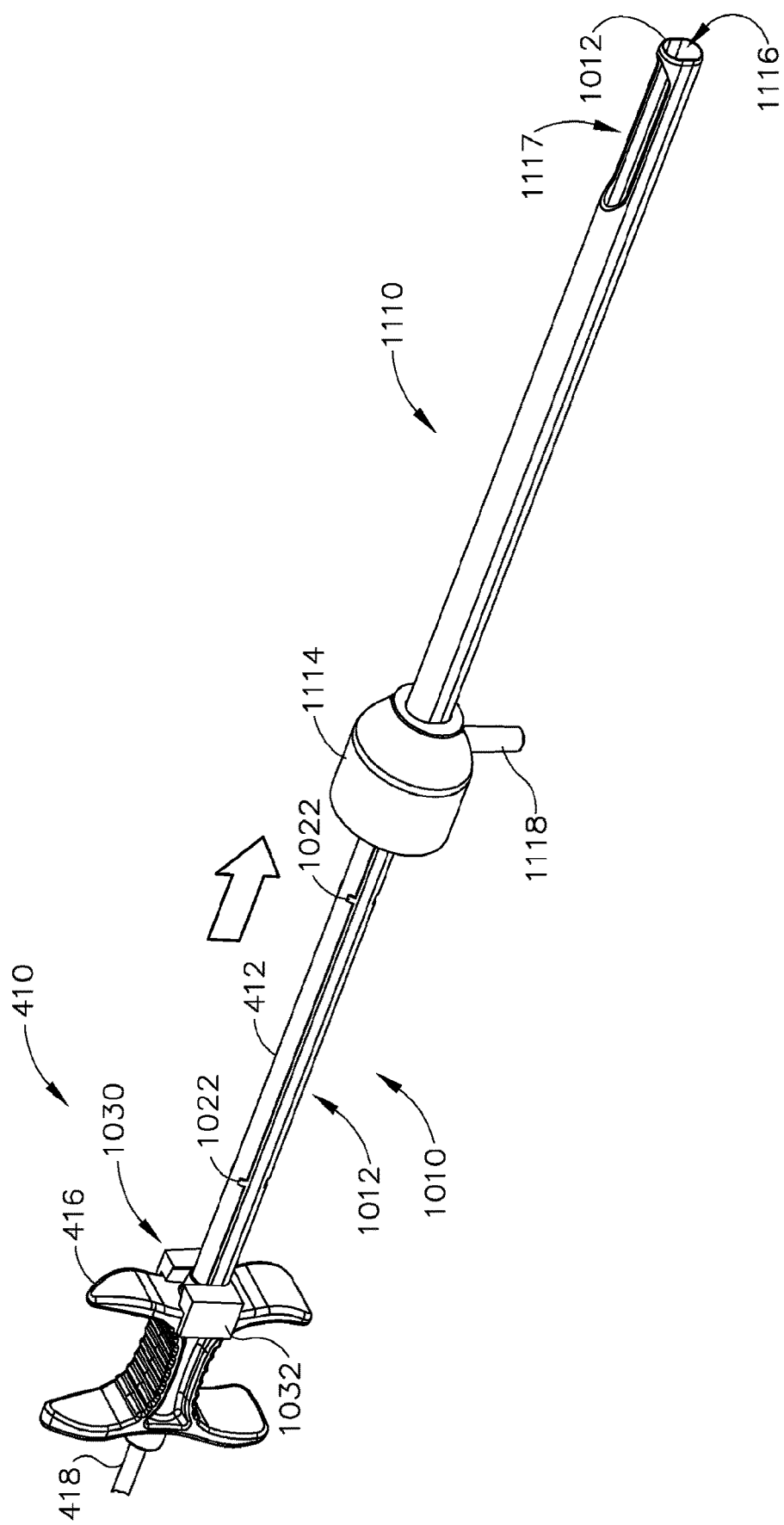
FIG. 21 depicts a perspective view of the cannula of FIG. 19, with the marker delivery device of FIG. 4 and the adaptor device of FIG. 7 partially inserted into the cannula.
Figure 22:
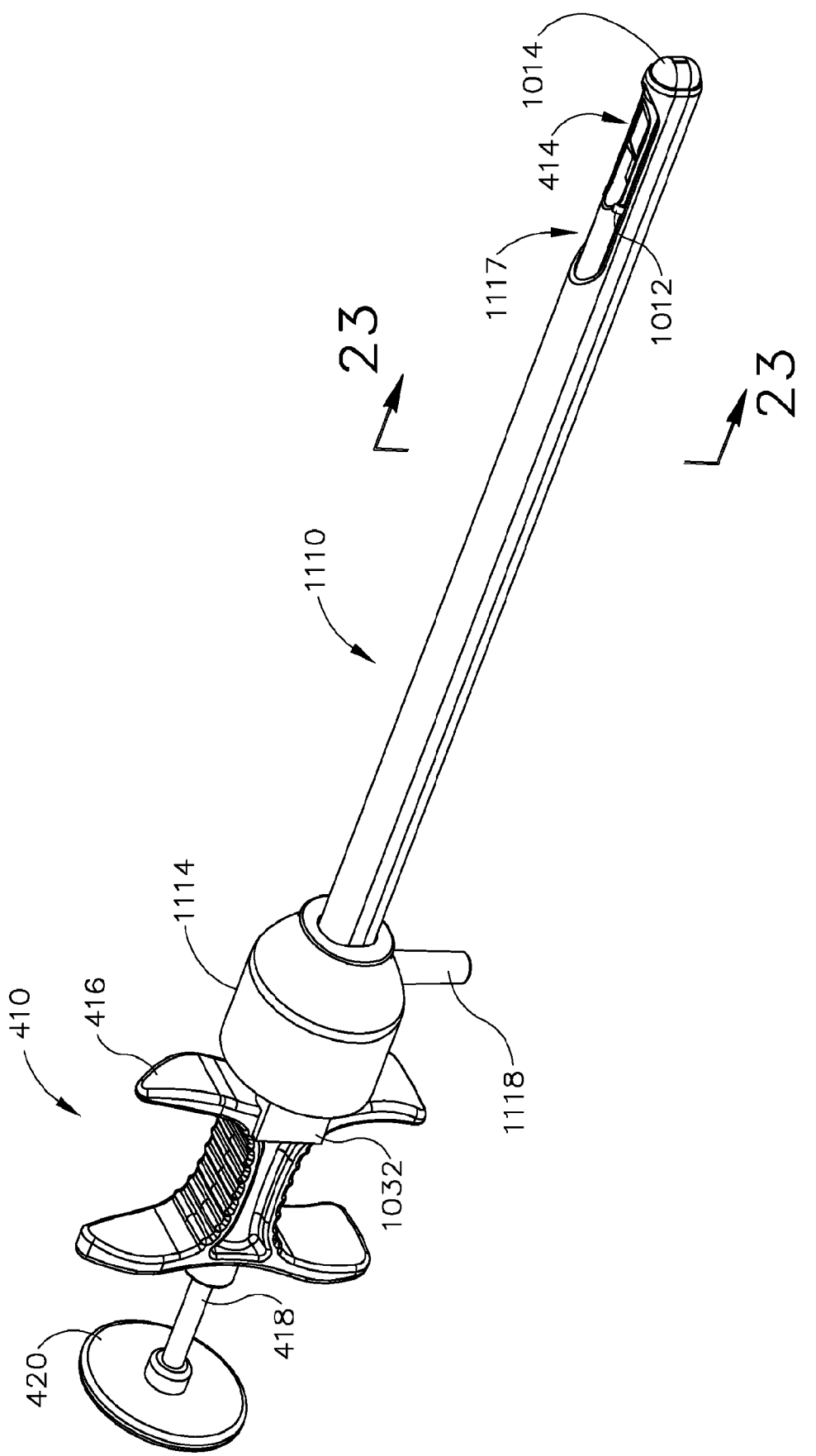
FIG. 22 depicts a perspective view of the cannula of FIG. 19, with the marker delivery device of FIG. 4 and the adaptor device of FIG. 7 fully inserted into the cannula.
Figure 23:
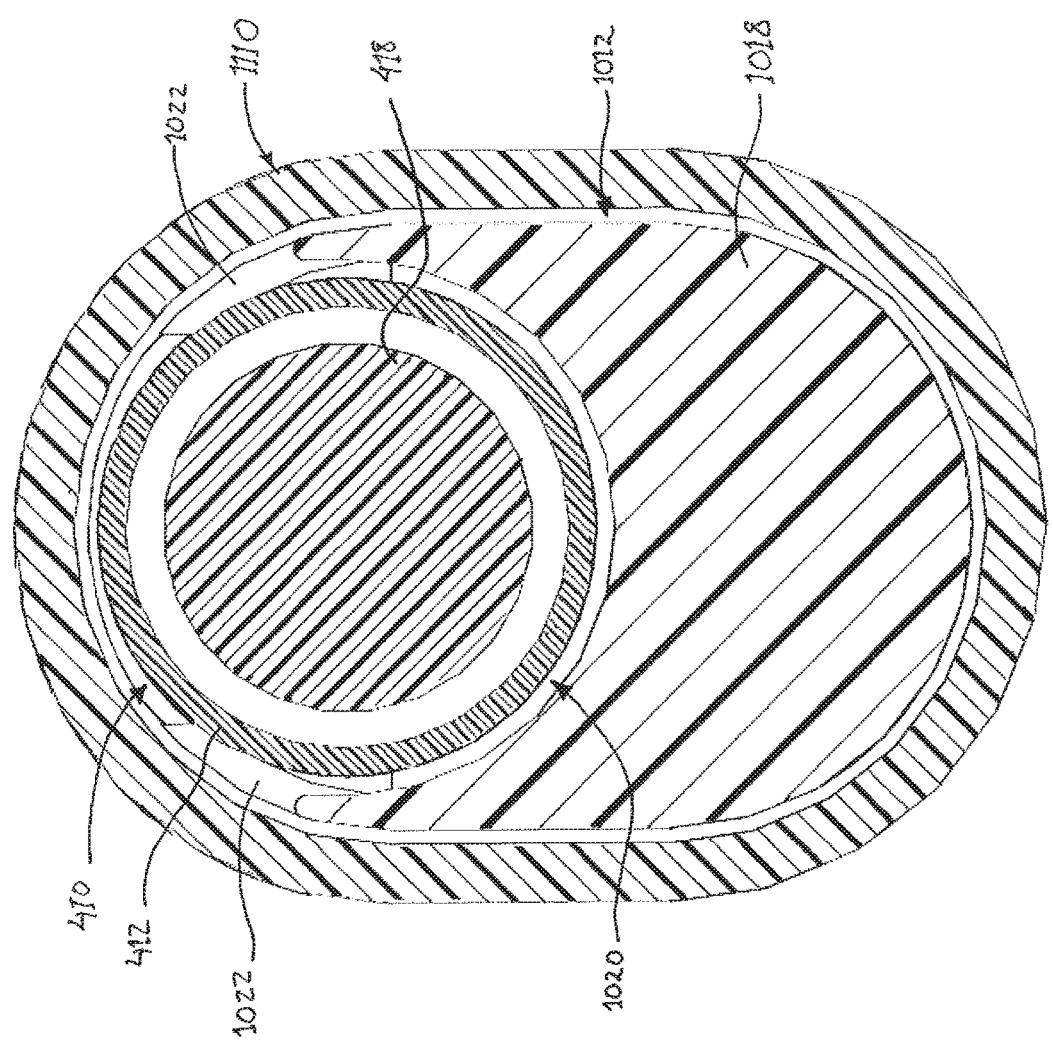
FIG. 23 depicts a side cross-sectional view of the cannula of FIG. 19, the marker delivery device of FIG. 4 and the adaptor device of FIG. 7, with the cross-section taken along line 23-23 of FIG. 22.

As can be seen in FIGS. 20 and 21, an operator may insert marker delivery device (410) with adaptor device (1010) into cannula (1110) by inserting distal tip (1014) of adaptor device (1010) into the proximal end of hub (1114), which is in communication with lumen (1116). As can be seen in FIG. 22, once marker delivery device (410) and adaptor device (1010) are fully inserted into cannula (1110), lateral aperture (414) of marker delivery device (410) is in alignment with lateral aperture (1117) of cannula (1110). In particular, longitudinally alignment is achieved because elongate sheath (1012) of adaptor device (1010) and outer cannula (412) of marker delivery device (410) each comprise lengths that correspond to the length of cannula (1110). As can best be seen in FIG. 23, angular alignment is achieved by the ovular cross-sectional shape defined by marker delivery device (410) together with adaptor device (1010). In particular, such a shape keys with the ovular shape of lumen (1116) of cannula (1110) to thereby align lateral aperture (414) of marker delivery device (410) and lateral aperture (1117) of cannula (1110). It should be understood that once marker delivery device (410) and adaptor device (1010) are fully inserted in cannula (1110), an operator may depress plunger (420) of marker delivery device (410) to thereby deploy marker (600) through lateral aperture (414) of marker delivery device (410) and lateral aperture (1117) of cannula (1110).

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art.

For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy system comprising:
   (a) a targeting set, wherein the targeting set includes a sleeve assembly defining a lumen;
   (b) a marker deployer, wherein the marker deployer comprises an elongate cannula, a plunger, and a handle, wherein the cannula extends distally from the handle and includes a lateral aperture, wherein at least a portion of the plunger is disposed within the cannula and is configured to selectively drive a marker through the lateral aperture of the cannula; and
   (c) an deployer adaptor, wherein the deployer adaptor is selectively attachable to the cannula of the marker deployer such that the deployer adaptor and the cannula together define a first cross-sectional shape, wherein the first cross-sectional shape corresponds to a second cross-sectional shape defined by the lumen of the sleeve assembly, wherein the deployer adaptor is operable to adapt the marker deployer for use with the sleeve assembly of the targeting set.

2. The biopsy system of claim 1, wherein the lumen of the sleeve assembly extends from a proximal end of the sleeve assembly to the distal end.

3. The biopsy system of claim 2, further comprising a biopsy device, wherein the biopsy device includes an elongate needle, wherein the needle is insertable into the lumen of the targeting set.

4. The biopsy system of claim 3, wherein the needle of the biopsy device comprises at least one lumen, wherein the at least one lumen has a third cross-sectional shape, wherein the cannula of the marker deployer is configured for insertion into the needle of the biopsy device.

5. The biopsy system of claim 4, wherein the cannula of the marker deployer has a fourth cross-sectional shape, wherein the fourth cross-sectional shape corresponds to the third cross-sectional shape.

6. The biopsy system of claim 5, wherein the second cross-sectional shape is different from the third cross-sectional shape.

7. The biopsy system of claim 6 wherein the first cross-sectional shape is oval-shaped.

8. The biopsy system of claim 6, wherein the second cross-sectional shape is circular.

9. The biopsy system of claim 1 wherein the deployer adaptor defines a deployer channel, wherein the deployer channel is configured to receive the cannula of the marker deployer.

10. The biopsy system of claim 1 wherein the deployer adaptor includes a plurality of snap features, wherein the snap features are configured to selectively secure the deployer adaptor to the marker deployer.

11. The biopsy system of claim 10, wherein the plurality of snap features comprises a cannula set and a handle set.

12. The biopsy system of claim 11, wherein the cannula set of the plurality of snap features is configured to engage with the cannula of the marker deployer to laterally secure the deployer adaptor to the marker deployer.

13. The biopsy system of claim 11 wherein the handle set of the plurality of snap features is configured to engage with the handle of the marker deployer to longitudinally secure the deployer adaptor to the marker deployer.

14. A biopsy system comprising:
   (a) a targeting set, wherein the targeting set comprises a cannula, wherein the cannula includes a lumen defining a first shape;
   (b) a marker delivery device, wherein the marker delivery device comprises an outer cannula, and a handle, wherein at least a portion of the outer cannula is configured to deliver a marker to a biopsy site, wherein the outer cannula is configured for insertion through a needle of a biopsy device;
   (c) an adaptor device wherein the adaptor device comprises an elongate sheath and an attachment member, wherein the sheath is associated with the outer cannula of the marker delivery device, wherein the attachment member is associated with the handle of the marker delivery device, wherein the adaptor device is configured to be selectively attachable to the marker delivery device such that the outer cannula of the marker delivery device and the elongate sheath define a second shape corresponding to the first shape, wherein the outer cannula of the marker delivery device is configured for insertion into the cannula of the targeting set when the adaptor device is attached to the marker delivery device.

15. The biopsy system of claim 14, wherein the marker delivery device and the adaptor device are configured for use during an MRI procedure.

16. The biopsy system of claim 14 wherein the adaptor device is configured to receive the marker delivery device such that the cannula of the marker delivery device is offset from a longitudinal axis of the sheath of the adaptor device.

17. The biopsy system of claim 14 wherein the adaptor device is selectively attachable to the marker delivery device by a plurality of resilient tabs.

18. A method for using a biopsy system comprising a targeting assembly including a sleeve assembly, a biopsy device, a marker delivery device, and an adaptor, wherein the method comprises:
   (a) introducing the sleeve assembly of the targeting assembly into tissue of a patient using an obturator inserted into the sleeve assembly;
   (b) removing the obturator from the sleeve assembly;
   (c) inserting at least a portion of the biopsy device into the sleeve assembly of the targeting assembly to collect a biopsy sample;
   (d) removing the biopsy device from the sleeve assembly of the targeting assembly after collecting a biopsy sample;
   (e) attaching the adaptor to at least a portion of the marker delivery device;
   (f) inserting the marker delivery device and at least a portion of the adaptor into the sleeve assembly of the targeting assembly while the marker delivery device is attached to the adaptor; and
   (g) using the marker delivery device to deploy a marker into tissue of a patient.

* * * * *